(12) United States Patent
Valliere-Douglass et al.

(10) Patent No.: US 9,958,455 B2
(45) Date of Patent: May 1, 2018

(54) INTACT MASS DETERMINATION OF PROTEIN CONJUGATED AGENT COMPOUNDS

(71) Applicant: Seattle Genetics, Inc., Bothell, WA (US)

(72) Inventors: John Fay Valliere-Douglass, Seattle, WA (US); Oscar Salas, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days. days.

(21) Appl. No.: 14/346,670

(22) PCT Filed: Sep. 27, 2012

(86) PCT No.: PCT/US2012/057649
§ 371 (c)(1),
(2) Date: Mar. 21, 2014

(87) PCT Pub. No.: WO2013/049410
PCT Pub. Date: Apr. 4, 2013

(65) Prior Publication Data
US 2014/0242624 A1    Aug. 28, 2014

Related U.S. Application Data

(60) Provisional application No. 61/540,839, filed on Sep. 29, 2011, provisional application No. 61/701,489, filed on Sep. 14, 2012.

(51) Int. Cl.
*C12Q 1/34* (2006.01)
*G01N 33/68* (2006.01)

(52) U.S. Cl.
CPC ........... *G01N 33/6848* (2013.01); *C12Q 1/34* (2013.01)

(58) Field of Classification Search
None
See application file for complete search history.

(56) References Cited

U.S. PATENT DOCUMENTS

2005/0232929 A1* 10/2005 Kadkhodayan .... C07K 16/2866
424/178.1

FOREIGN PATENT DOCUMENTS

JP    2007532882 A    11/2007
WO    2005/101017 A1    10/2005

OTHER PUBLICATIONS

Kükrer et al., Pharm. Res. 27: 2197-2204 (2010; published online Aug. 3, 2010).*

(Continued)

*Primary Examiner* — Erin M. Bowers
(74) *Attorney, Agent, or Firm* — Mintz Levin Cohn Ferris Glovsky and Popeo PC

(57) ABSTRACT

The present invention provides methods and systems for the rapid determination of the intact mass of non-covalently associated antibody heavy chains (HC) and light chains (LC) which result from the attachment of drug conjugates to interchain cysteine residues. By analyzing the antibody-drug conjugate (ADC) using native desalting conditions, the intact-bivalent structure of the ADC, which ordinarily would decompose as a consequence of denaturing chromatographic conditions typically used for LCMS, is maintained. The mass of the desalted ADC is subsequently determined using desolvation and ionization ESI-MS conditions. The methods described herein provide for direct measurement of the intact mass of an ADC conjugated at interchain cysteine residues. The methods described herein also provide for the relative quantitation of the individual ADC species.

34 Claims, 19 Drawing Sheets

(56) References Cited

OTHER PUBLICATIONS

Brady et al., J. Am. Soc. Mass Spectrom. 19: 502-509 (2008).*
Alpert et al., ABRF 2004 Poster #P55-S, http://www.polylc.com/downloads/ABRF_2004_poster.pdf, accessed Nov. 5, 2015.*
Brady, Lowell J. et al., "Molecular Mass Analysis of Antibodies by On-Line SEC-MS," *J Am Soc Mass Spectrom* (2008) 19:502-509.
International Search Report corresponding to PCT/US2012/057649 dated Dec. 18, 2012 (2 pagse).
Kosloski, Matthew P. et al., "Role of Glycosylation in Conformational Stability, Activity, Macromolecular Interaction and Immunogenicity of Recominbant Human Factor VIII," *The AAPS Journal* (Sep. 2009) 11(3):424-431.
Kukrer, Basak et al., "Mass Spectrometric Analysis of Intact Human Monoclonal Antibody Aggregates Fractionated by Size-Exclusion Chromatography," *Pharm Res* (2010) 27:2197-2204.
Liu, Hongcheng et al., "Analysis of Reduced Monoclonal Antibodies Using Size Exclusion Chromatography Coupled with Mass Spectrometry," *J Am Soc Mass Spectrom* (2009) 20:2258-2264.
Yamamoto, Nobuto et al., "Deglycosylation of Serum Vitamin $D_3$-binding Protein Leads to Immunosuppression in Cancer Patients," *Cancer Research* (Jun. 15 1996) 56:2827-2831.
Lazar, Alexandru C. et al., "Analysis of the composition of immunoconjugates using size-exclusion chromatography coupled to mass spectrometry," *Rapid Commun. Mass. Spectrom.* (Jun. 8, 2005) 19:1806-1814.
Extended European Search Report corresponding to EP12834802.6 dated Apr. 28, 2015; 7 pages.
Pinkse, Maitijn W. H. et al., "Probing Noncovalent Protein-Ligand Interactions of the cGMP-Dependent Protein Kinase Using Electrospray Ionization Time of Flight Mass Spectrometry," *J. Am. Soc. Mass. Spectrom.* (Accepted Jun. 29, 2004); 15:1392-1399.
Rose, Rebecca J. et al., "Quantitative Analysis of the Interaction Strength and Dynamics of Human IgG4 Half Molecules by Native Mass Spectrometry," *Structure* (Sep. 7, 2011); 19:1274-1282.
Third Party Observation filed for EP Application No. 20120834802 on Oct. 16, 2017; EPO Formal Communication pursuant to Rule 114(2)EPC dated Oct. 23, 2017; 9 pages.
TOSOH Corporation Instruction Manual *Packed Column for Aqueous High Performance GFC; TSKgel SW Type* (Revised Oct. 2010); 20 pages.
Valliere-Douglass, John F. et al., "Native Intact Mass Determination of Antibodies Conjugated with Monomethyl Auristatin E and F at Interchain Cysteine Residues," *Anal. Chem.* (Feb. 15, 2012); 84(6):2843-2849.
Wakankar, Aditya et al., "Analytical methods for physicochemical characterization of antibody drug conjugates," *mAbs* (published online: Mar. 1, 2011); 3(2):161-172, DOI: 10.4161/mabs.3.2.14960.

* cited by examiner

A.

B.

INTACT MASS DETERMINATION OF PROTEIN CONJUGATED AGENT COMPOUNDS

CROSS-REFERENCES TO RELATED APPLICATIONS

This application claims priority to, and the benefit of, U.S. Provisional Patent Application Ser. No. 61/540,839, filed Sep. 29, 2011, and U.S. Provisional Patent Application Ser. No. 61/701,489, filed Sep. 12, 2012, the disclosures of which are incorporated herein by reference in their entirety.

BACKGROUND OF THE INVENTION

Antibody Drug Conjugates (ADC) are compounds for the targeted delivery of payloads to a target. In many instances, the target is a tumor associated antigen (TAA) and the payload is a drug.

There are a variety of classes of antibodies including IgG1 and IgG2. The structure of an IgG1 and IgG2 antibody includes 2 heavy chains (HC) and 2 light chains (LC). The two heavy chains and two light chains presented as a complex comprise an intact antibody. Each IgG1 antibody has 12 intrachain and 4 interchain disulfide bonds created through the oxidation of their respective cysteines on each antibody chain. There are two disulfide bonds between the heavy chain and light chains and two disulfide bonds between the heavy chain and the heavy chain. Complete reduction of the interchain disulfide bonds of an IgG1 antibody results in the antibody complex being maintained through non covalent interactions.

Complete reduction of the interchain disulfide bonds of an IgG1 antibody yields eight accessible thiols for conjugation with a drug, generally via a linker. By varying the reduction parameters, antibody isomers with from 0 to 8 thiols available for conjugation can be obtained. For example, reducing an IgG1 with DTT can yield antibodies with 2, 4, 6, or 8 accessible thiols. Fully reduced ADCs are held together by non-covalent interactions, such as hydrogen bonds, ionic bonds, hydrophobic, and van der Waal's interactions, and will separate into light and heavy chains under denaturing conditions (e.g., reverse phase chromatography). Non fully reduced ADCs are held together by covalent and non covalent interactions. The portions of non-fully reduced ADCs held together by covalent means may also be separated under denaturing conditions.

Fully loaded IgG1 ADCs have one drug molecule attached to each cysteine that makes up the interchain disulfides of an antibody for a total of eight drugs per antibody. Partially loaded ADCs generally have 2, 4, or 6 drug molecules attached to cysteine residues. Partially loaded ADCs are also observed to have 1, 3, and 5 drug molecules attached to cysteine residues. While the mass of the constituent fragments of loaded ADCs have been assayed by mass spectrometry (MS), there remains a problem in the field to which the present invention relates regarding assaying the mass of the intact loaded ADC.

Although techniques for directly measuring the mass of an intact loaded ADC are lacking, various indirect means for measuring the mass of loaded ADCs are known. For example, the mass of an ADC has been measured by binding a sample (e.g., an ADC) to a heated reversed phase-high pressure liquid chromatographic column (rp-HPLC) in the presence of low or no organic solvent which typically also contains an ion pairing acid (e.g., trifluoracetic acid) and allows the non-volatile salts and surfactants to be washed from the sample (commonly referred to as desalting). In this example, the protein is eluted from the rp-HPLC column by increasing the organic content of the solvent to the point at which the interactions between the hydrophobic protein domains and the surface of the rp-HPLC column are disrupted by a non-polar organic solvent. An undesirable effect of this technique is that it destroys the protein structure by subjecting the protein samples to heat, acid and organic solvent, any one of which can denature proteins and destroy the protein structure. When non-covalent protein complexes are subjected to rp-HPLC they fall apart into their constituent covalent entities. the case of an IgG1 antibody with 8 interchain linked cysteine drugs, desalting on a rp-HPLC column results in complete dissociation of the ADC into heavy chains with 3 drugs per chain and light chains with 1 drug per chain. While the mass of the constituent fragments can be determined by mass spectrometry (MS), techniques for determining the mass of the intact entity are lacking in the field to which the present invention pertains.

Current MS techniques are lacking for measuring the mass of intact ACDs due, in part, to the fact that these techniques lead to protein denaturation and/or are too time consuming for the uses contemplated herein. Virtually all methods of native electrospray ionization (ESI) MS of proteins specify that this procedure should be carried out at nanospray scale (flow rate of 100 to 500 nanoliters/minute) to minimize the disruption to protein structure that would occur from heated sheath and desolvation gases that are used for standard ESI. The sample handling process for measuring the native mass of an ADC using conventional nanospray ESI-MS techniques is very time consuming and not amenable to high throughput. Not including the time to deglycosylate the antibody, it takes at least an hour per sample to obtain a mass measurement, Furthermore, previously known methods for analyzing interchain cysteinyl-linked ADC's are either not amenable to on-line mass spectrometry HIC) or result in the denaturing dissociation of conjugated heavy and light chains during chromatographic separation and subsequent mass measurement (e.g., rp-HPLC). Therefore, there is a need in the field to which the instant invention pertains related to methods for routinely and rapidly determining the intact mass of a cysteine-linked ADC.

Surprisingly, the present invention meets this need as well as other unmet needs in the relevant field by providing methods, devices, and systems for detecting the mass of a non covalently associated protein agent conjugate.

BRIEF SUMMARY OF THE INVENTION

In one aspect, the present inventions provides a method for detecting a mass of a protein agent conjugate. The method includes the steps of providing a non covalently associated and non denatured protein agent conjugate compound in a volatile salt and free of a non-volatile salts; introducing the protein agent conjugate compound into a mass spectrometer; and directly establishing the mass of the protein agent conjugate compound by mass spectrometry.

In a second aspect, the present invention provides systems, such as, but not limited to, a mass spectrometer that is configured to perform one of the methods described herein.

DETAILED DESCRIPTION OF THE INVENTION

I. General

Figure 1:
FIG. 1 shows the IgG1 structures of various representative ADC's with MR from 0 to 8 including the isomers produced by conjugation of an antibody with an agent which is, in one aspect, a drug, in another aspect, a label, and in yet another aspect, a toxin. Disulfide linkages between subunits of the antibody (designated mAb in the figure) (MR=0) are linked to drugs in the ADC resulting in non-covalently associated 2LC-2HC drug-linked species.
Figure 2A:
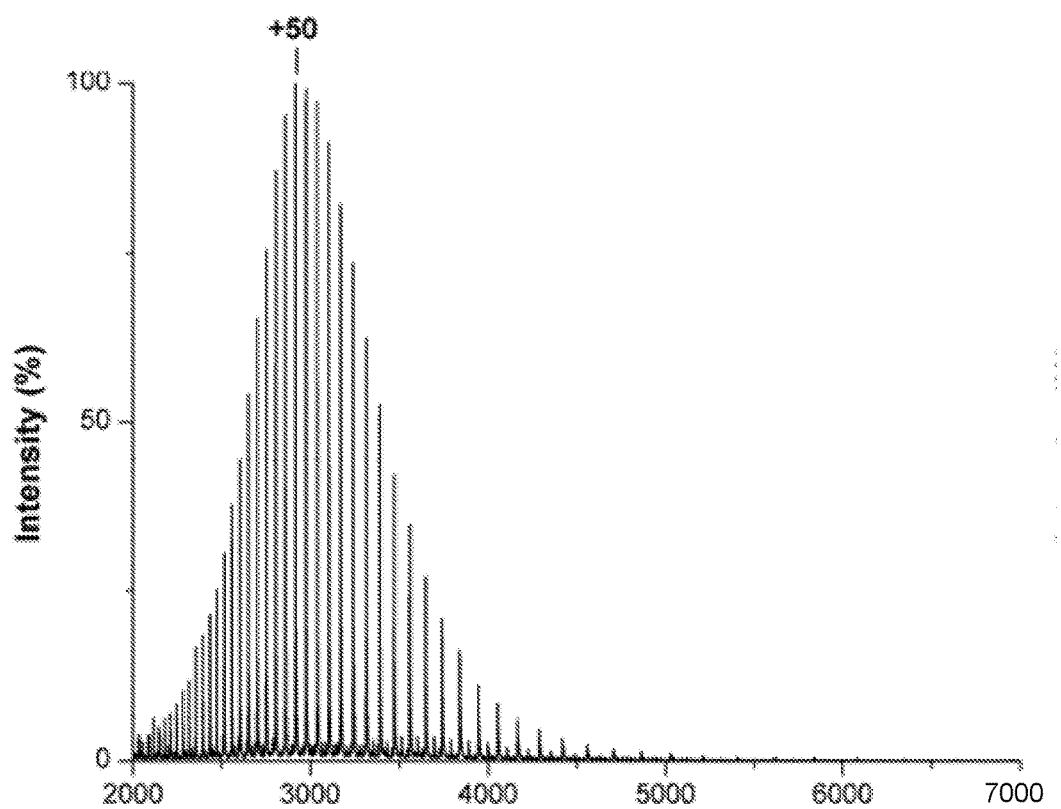
FIG. 2 shows the unprocessed and deconvoluted MS associated with mass measurement of deglycosylated mAb-A in denaturing and non-denaturing conditions. The unprocessed and deconvoluted MS data obtained in denaturing conditions are shown in panels A and C, respectively, and the unprocessed and deconvoluted MS data Obtained in non-denaturing conditions are shown in panels B and D, respectively. The ions evident between 200 and 3500 m/z in panel B which is the region in which denatured antibody would be evident are due to the presence of PNGase F which was used for deglycosylation and the non-ionic detergent Tween-80.
Figure 2B:
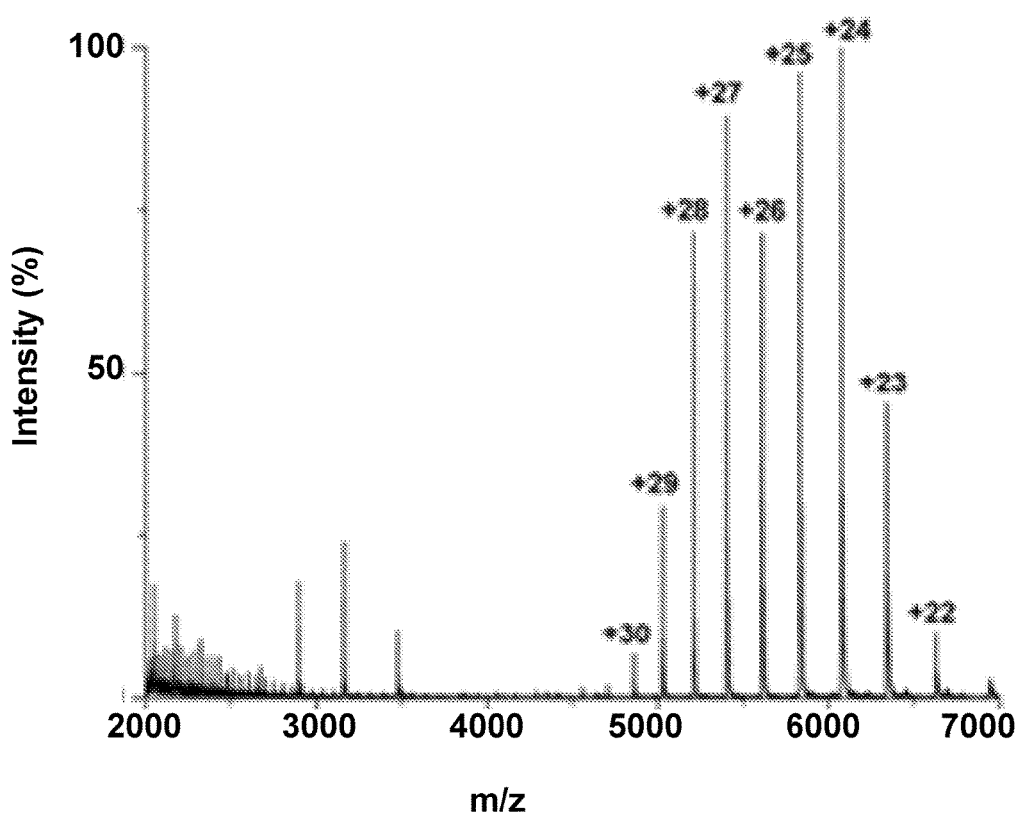
Figure 2C:
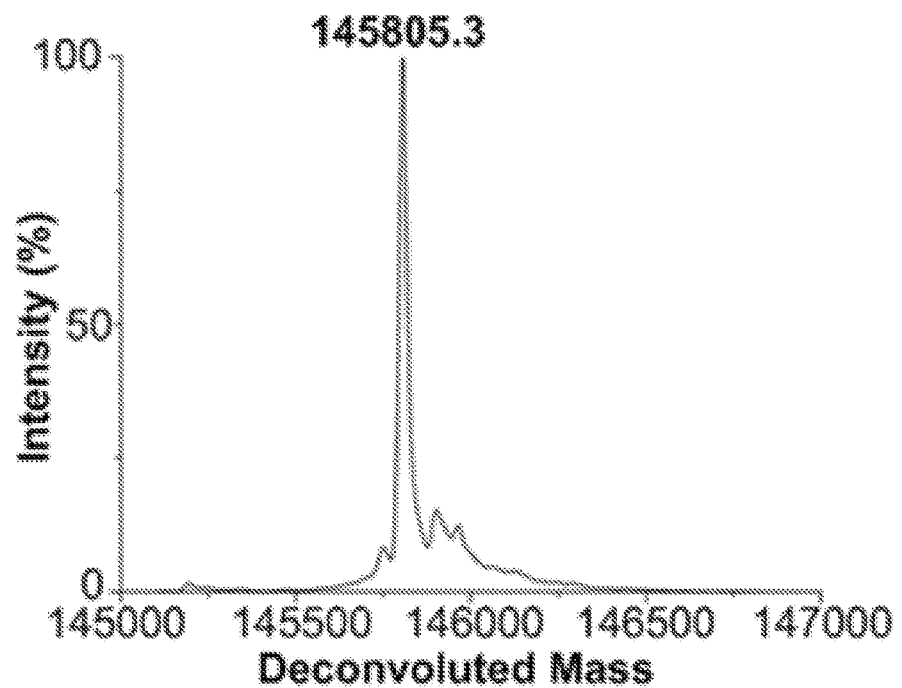
Figure 2D:
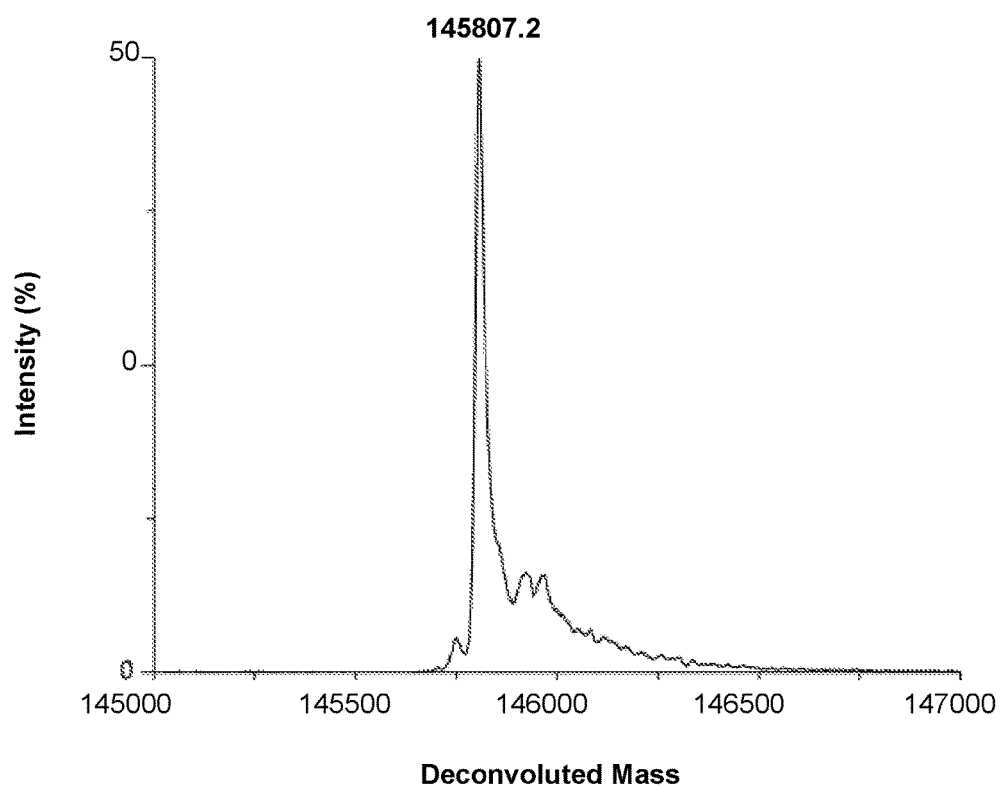
Figure 3A:
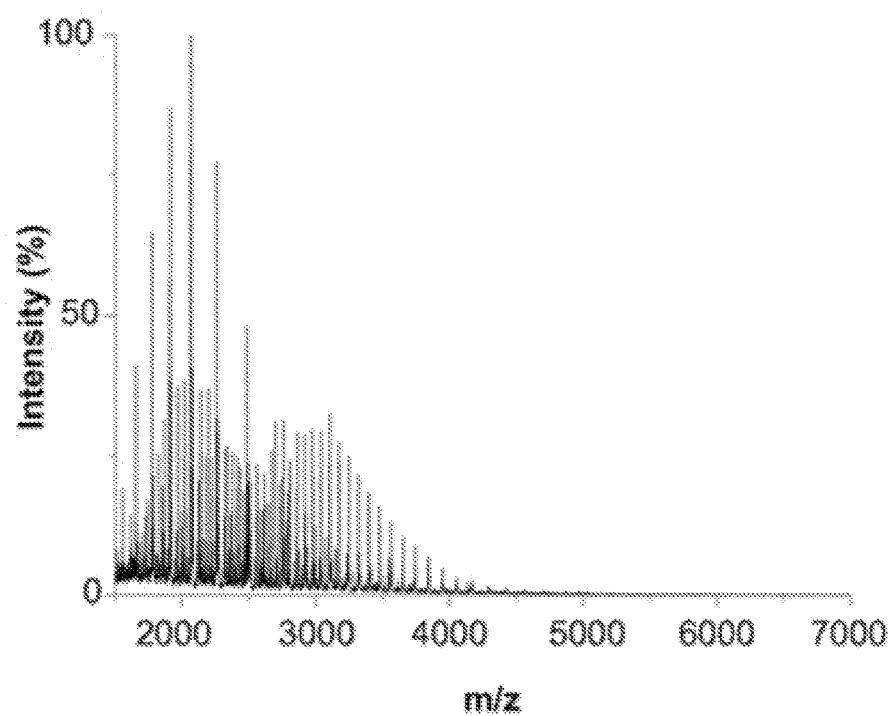
FIG. 3 shows the unprocessed and deconvoluted MS associated with mass measurement of a deglycosylated maleimidocaproyl monomethyl auristatin F (mcMMAF) conjugate ADC-A in denaturing and non-denaturing conditions. The unprocessed and deconvoluted MS data obtained in denaturing conditions are shown in panels A and C, respectively, and the unprocessed and deconvoluted MS data obtained in non-denaturing conditions is shown in panels B and D, respectively. Multiply charged ions for intact ADC-A are indicated with a bracket in panel B and deconvolution artifacts present in panels C and D are indicated with asterisks.
Figure 3B:
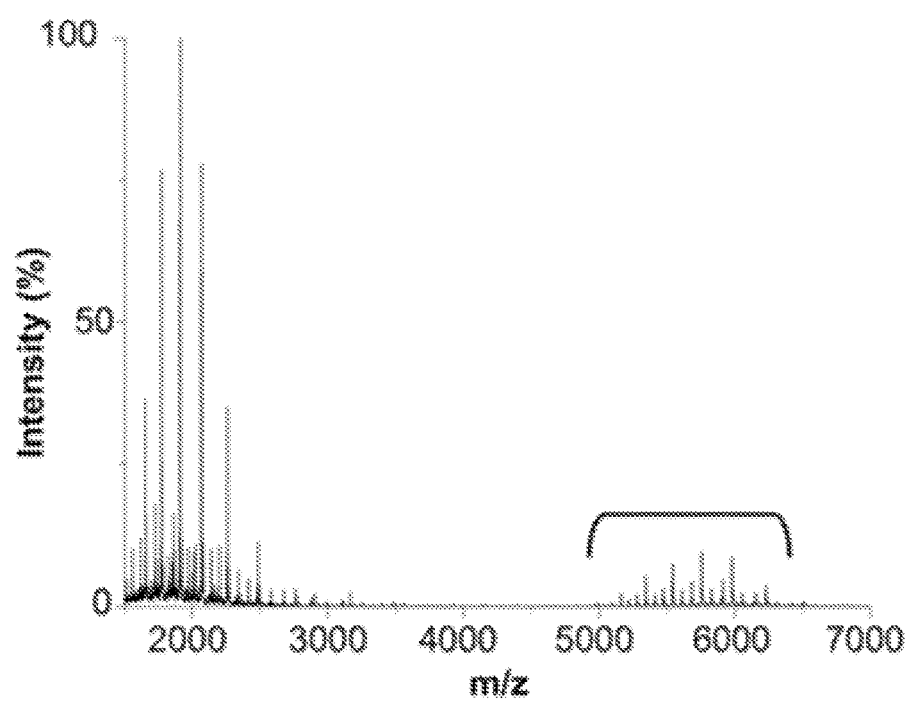
Figure 3C:
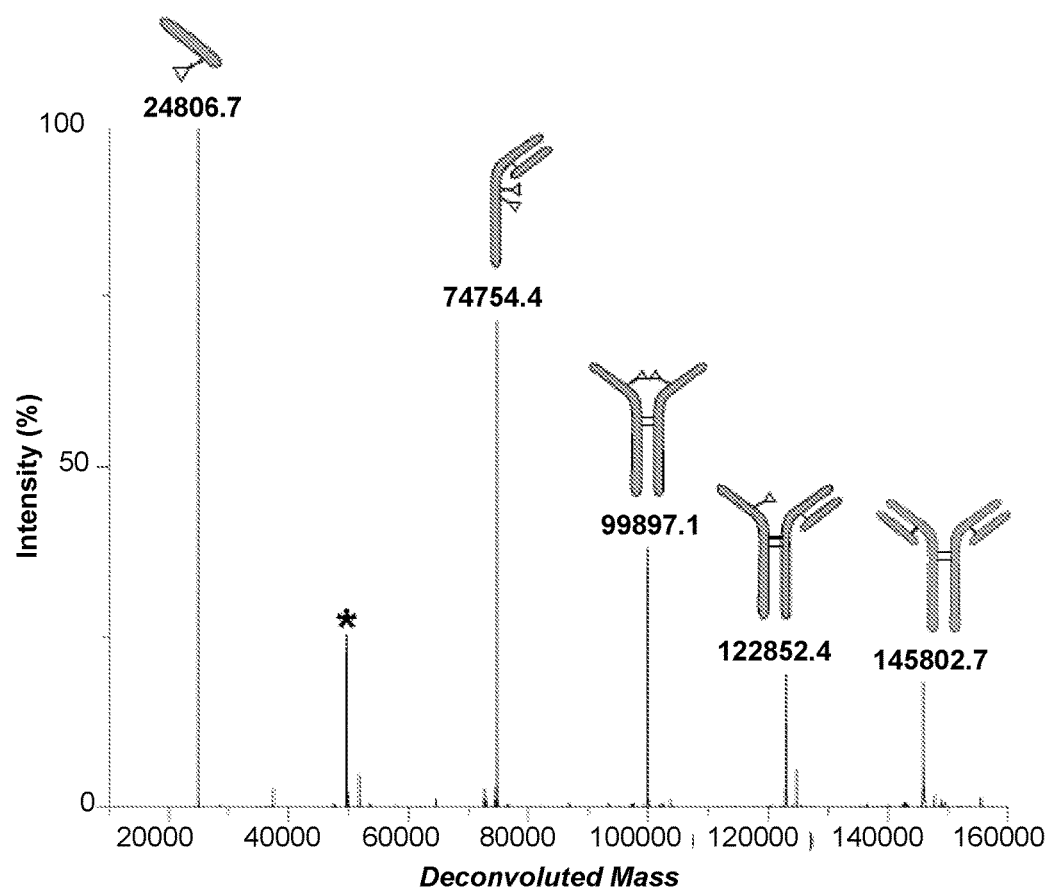
Figure 3D:
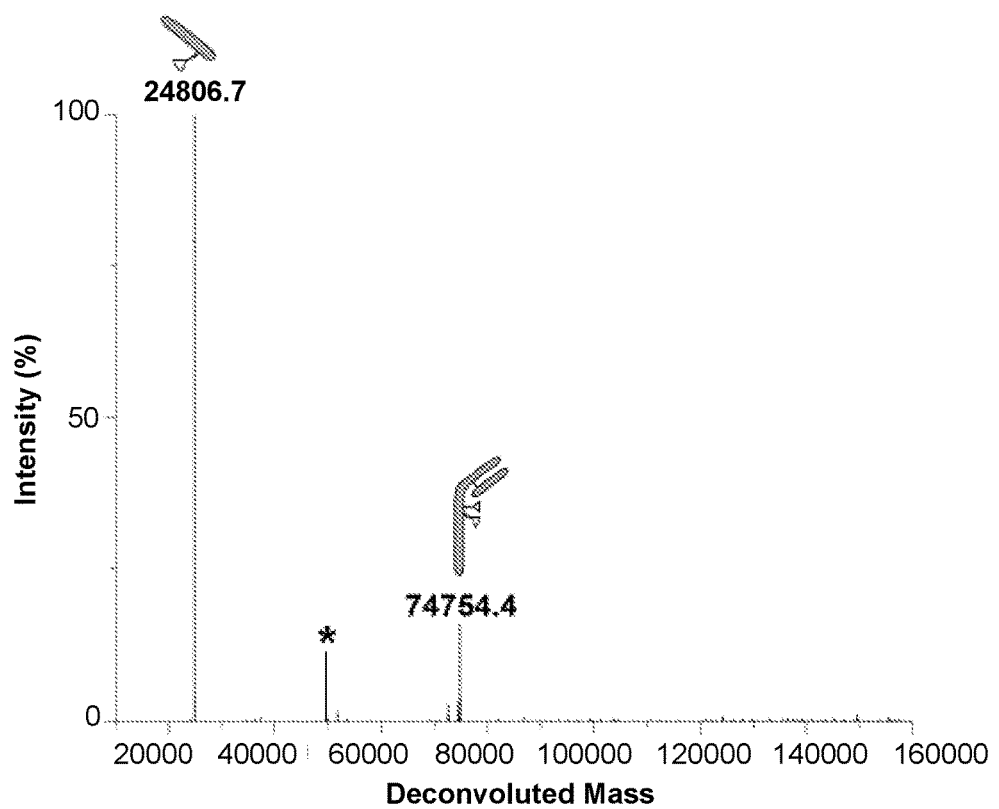

The present invention sets forth methods for detecting the mass of a non covalently associated protein agent conjugate compound. These methods include the steps of: (a) providing a protein agent conjugate compound in a matrix; (b) introducing the eluted protein agent conjugate compound into a mass spectrometer; and (c) directly establishing the mass of the protein agent conjugate compound by mass spectrometry. In further embodiments, a separation media is applied under non denaturing conditions for the protein agent conjugate compound in the matrix to effect separation of the protein agent conjugate compound from the matrix. In some of these embodiments, the protein agent conjugate compound is substantially non-denatured. In yet further embodiments, the non denatured protein agent conjugate compound is eluted from the separation media compound in a volatile salt.

I. Definitions

Unless otherwise defined, all terms of art, notations and other scientific terms or terminology used herein are intended to have the meanings commonly understood by those of skill in the art to which this invention pertains. In some cases, terms with commonly understood meanings are defined herein fir clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

When trade names are used herein, it is intended to independently include the trade name product formulation, the generic drug, and the active pharmaceutical ingredient(s) of the trade name product.

As used herein, the abbreviation "MR" refers to the number of drug molecules conjugated to, for example, the protein or the antibody. For example, MR=0 means that zero drug molecules are conjugated to a given protein or a given antibody. MR=8 means that there are eight drug molecules conjugated to it given protein or a given antibody. MR may include 0, 1, 2, 3, 4, 5, 6, 7, and 8.

Unless stated otherwise, the following terms and phrases as used herein are intended to have the following meanings:

As used herein, the term "ADC" refers to an antibody drug conjugate. The antibody portion of the ADC has specificity for an antigen. Antigens of interest include, but are not limited to, CD30, CD40, CD19, CD33 and CD70.

As used herein, the term "protein" refers to compounds comprising one or more polypeptides typically folded into a three dimensional form, and which may facilitate a biological function.

As used herein, the term "polypeptide" refers to a polymer of amino acids and its equivalent and does not refer to a specific length of a product; thus, "peptides" and "proteins" are included within the definition of a polypeptide. Also included within the definition of proteins are "antibodies" as defined herein. A "polypeptide region" refers to a segment of a polypeptide, which segment may contain, for example, one or more domains or motifs (e.g., a polypeptide region of an antibody can contain, for example, one or more CDRs).

As used herein, the term "fragment" refers to a portion of a polypeptide typically having at least 20 contiguous or at least 50 contiguous amino acids of the polypeptide.

As used herein, the phrase "non covalently associated protein" refers to a protein in which at least one covalent association between polypeptide chains is disrupted and which maintains its intact tertiary or quaternary structure. For example, with reference to an ADC, a non covalently associated protein is a protein which has undergone reduction of its interchain disulfide bonds while maintaining its intact structure (i.e., the two heavy chains remain associated with the two light chains). ADC's are composites of covalent and non-covalent interactions. Covalent interactions are maintained in some ADCs, for example, those ADCs which have 2, 4, or 6 drug loadings. in an example of an ADC which has a 2 drug load, the ADC has covalent inter-chain disulfides between both heavy chains and one light chain-heavy chain with the other light chain-heavy chain present as a non-covalent structure likewise, in an example of a 4 drug loaded ADC, it is also a composite of covalent and non-covalent interactions between the heavy and light chains.

As used herein, the phrase "protein agent conjugate compound" refers to a compound including a protein conjugated to an agent. The protein may be, but is not limited to, an antibody, antibody fragment, an Fc fusion protein, or a non-covalent protein complex. In some aspects, the protein may be an antibody. in another aspect, the protein is an antibody fragment. In other aspects, the protein may be an Fc fusion protein. In yet other aspects, the protein may be composed of a complex of subunits not bound by covalent bonds. Examples of these types of proteins are hemoglobin which is tetrameric assembly of 2 alpha and 2 beta chains associated non-covalently, Concanavalin A which is a tetramer, and estrogen receptor which is a dimer. Fc fusion proteins involve grafting of a functional protein or protein domain to an Fc dimer whereby the Fc monomers are bound by cysteine residues in the hinge region of the The protein may have quaternary structure which is not held together by covalent bonds but only by non-covalent interactions. An example is hemoglobin which is comprised of 4 subunits that can be dissociated under denaturing conditions. The cysteines of hemoglobin may be conjugated with drugs, but, in contrast to antibodies, the cysteines are not actually participating in covalently binding together the subunit structure.

As used herein, the term refers to a drug, label, toxin or the like.

As used herein, the term "matrix" refers to the context or milieu in which a protein or protein agent conjugate compound is present. For example, a "matrix" includes formulation buffers, biological serum, surfactants, excipients or cell culture media.

As used herein, the phrase "non denaturing condition" refers to a condition where proteins (e.g., antibodies) do not lose their secondary, tertiary or quaternary structures. Non-denaturing conditions include the absence of heat in excess of the level that would cause thermal unfolding (e.g., 50° C. or greater) and pH extremes (for example, below pH 5 and above pH 8).

As used herein, the phrase "non denatured protein" means a protein (e.g., an antibody) which has maintained its secondary, tertiary and, where applicable, quaternary structures.

As used herein, the term "reduced protein" (e.g., an antibody) refers to a protein in which its interchain disulfide bonds have been broken.

As used herein, the phrase "denatured protein" (e.g., an antibody) is one in which the protein has lost its secondary, tertiary or quaternary structure.

As used herein, the term "substantially" means 1%, 2%, 3%, 4%, 5%, 6%, 7%, 8%, 9%, or 10% of the amount measured by the relative levels of the molar ratios as determined by MS based quantitation from the deconvoluted mass spectrum and by UV integration of the species separated by HIC, which proteins e.g., antibody) are not denatured following the separation media step (for example, by SEC).

As used herein, the term "eluent" refers to the liquid mobile phase that dissociates analytes from the chromatography column stationary phase. Analytes include, but are not limited to, compound(s) of interest to be measured.

As used herein, the term "directly" refers to the context for establishing the mass of a protein (including a protein agent conjugate compound) which includes measuring the mass of the entire quaternary ensemble, e.g., the intact entity, such as an antibody complex.

As used herein, the term "indirectly" means measuring the mass of the protein (including a protein agent conjugate compound) by measuring the masses of the subunits that comprise the quaternary ensemble, e.g., the light and heavy chains of an antibody, and adding those masses together to arrive at a number for the intact entity.

"Desalting" refers to separating a protein (including a protein agent conjugate compound) sample from non-volatile salts, excipients and/or surfactants.

A "volatile salt" refers to a salt that enter the gas phase at ambient environmental pressure (1 atmosphere). Volatile salts include, for example, ammonium formate, ammonium acetate, ammonium carbonate.

A "surfactant" includes, but is not limited to, non-volatile compounds of the matrix. For example, surfactants include non-ionic and zwitterionic detergents, such as polysorbate 20 ("tween 20") and polysorbate 80 ("tween 80").

A "chaotropic agent" refers to a chemical which destabilizes hydrogen bonds, van der Waals forces and hydrophobic interactions between proteins and between subdomains within a protein and subsequently results in denaturation. Exemplary compounds include, but are not limited to, guanidine-HCl, urea, and other compounds known to one of skill in the art.

An "excipient" includes compounds such as sugars and polyols, for example, sucrose, trehalose, and sorbitol.

"Mass spectrometry" (MS) is an analytical technique used to measure the mass to charge ratio of charged particles. It may be used for elucidating the primary structure of proteins.

"Liquid chromatography" or "LC" refers to a method for the separation of mixtures. The mixture is dissolved in a fluid called the mobile phase which carries it through a structure called the stationary phase. In the case of size exclusion chromatography (SEC) the various constituents of the mixture travel at varying speeds, causing them to separate. The separation is based on differential partitioning between the mobile and stationary phases.

"Size exclusion chromatography" (SEC) refers to a chromatographic method in which molecules are separated by their size and not by another separation parameter such as molecular weight or polarity. It is applied to large molecules such as proteins. In size exclusion chromatography, salts are primarily used as a mobile phase. In some instances, organic and chaotropic agents can be also present in the mobile phase. The stationary phase is usually, but not limited to, one of the following: crosslinked polystyrene, derivitized silica, acrylic, hydroxylated acrylic, acrylic, agarose, or a polyhydroxyethyl-aspartamide backbone. The resin backbone may be derivitized with any number of species and the choice of derivitizing agent is typically driven by a need to reduce unwanted molecular interactions between the analyte to be separated and the column that would be employed in a separation method based on a separation parameter other than the compound's size.

As used herein, the phrase "mass spectrometry compatible volatile SEC buffer" refers to a mobile phase for an SEC which is compatible for use with the MS.

As used herein, the term "antibody" refers in the broadest sense to antibody, as used in the relevant field to which the present invention pertains, and specifically covers monoclonal antibodies, polyclonal antibodies, multispecific antibodies (e.g., bispecific antibodies), and antibody fragments. Antibodies may be murine, human, humanized, chimeric, or derived from other species.

As used herein, the term "antibody," also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cells or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule.

As used herein, the terms "antibody fragments" include, but are not limited to, a portion of a full length antibody, generally the antigen binding or variable region thereof. Examples of antibody fragments include Fab, Fab', F(ab')$_2$, and F$_v$ fragments; Fc, half Fc (½ FC), diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens; single-chain antibody molecules; and multispecific antibodies formed from antibody fragments.

As used herein, an "intact antibody" refers to antibody including the VL and VH domains, as well as complete light and heavy chain constant domains and remaining associated through at least one non covalent interaction. An "intact antibody fragment" includes a portion of a full length antibody remaining associated through at least one non covalent interaction.

The term "interchain disulfide bond," in the context of an antibody, refers to a disulfide bond between two heavy chains, or a heavy and a light chain.

The term "intrachain disulfide bond" in the context of the antibody, refers to a disulfide bond formed from 2 cysteine residues on the same polypeptide chain.

The term "interchain thiol" refers to a thiol group of an antibody heavy or light chain that can participate in the formation of an interchain disulfide bond.

The term "monoclonal antibody" or "mAbs" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies.

The intact antibody may have one or more "effector functions" which refer to those biological activities attributable to the Fc region (a native sequence Fc region or amino acid sequence variant Fc region) of an antibody. Examples of antibody effector functions include, but are not limited to, C1q binding; complement dependent cytotoxicity; Fc receptor binding; antibody-dependent cell-mediated cytotoxicity (ADCC); phagocytosis; and down regulation of cell surface receptors B cell receptor; BCR).

The antibody may be a fusion protein of an antibody, or a functionally active fragment thereof. For example, the antibody may be fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

The term "fusion protein" as used herein may also refer in context to binding domain-Ig fusions, wherein the binding domain may be, for example, a ligand, an extracellular domain of a receptor, a peptide, a non-naturally occurring peptide or the like, with the proviso that the binding domain does not include a variable domain of an antibody. Like the proteins and antibodies described herein, the Ig portion of the fusion protein must comprise at least one reducible disulfide bond. In one aspect, the Ig domain will be the Fc region of an antibody. Examples of domain-Ig fusion proteins include etanercept which is a fusion protein of sTNFRII with the Fc region (U.S. Pat. No. 5,605,690), alefacept which is a fusion protein of LFA-3 expressed on antigen presenting cells with the Fc region (U.S. Pat. No. 5,914,111), a fusion protein of Cytotoxic T Lymphocyte-associated antigen-4 (CTLA-4) with the Fc region (J. Exp. Med. 181:1869 (1995)), a fusion protein of interleukin 15 with the Fc region (J. Immunol. 160:5742 (1998)), a fusion protein of factor VII with the Fc region (Proc. Natl. Acad. Sci. USA 98:12180 (2001)), a fusion protein of interleukin 10 with the Fc region (J. Immunol. 154:5590 (1995)), a fusion protein of interleukin 7 with the Fc region (J. Immunol. 146:915 (1991)), a fusion protein of CD40 with the Fc region (Surgery 132:149 (2002)), a fusion protein of Flt-3 (fms-like tyrosine kinase) with the antibody Fc region (Acta. Haemato. 95:218 (1996)), a fusion protein of OX40 with the antibody Fc region (J. Leu. Biol. 72:522 (2002)), and fusion proteins with other CD molecules (e.g., CD2, CD30 (TNFRSF8), CD95 (Fas), CD106 (VCAM-1), CD137), adhesion molecules (e.g., ALCAM (activated leukocyte cell adhesion molecule), cadherins, ICAM (intercellular adhesion molecule)-1, ICAM-2, ICAM-3) cytokine receptors (e.g., interleukin-4R, interleukin-5R, interleukin-6R, interleukin-9R, interleukin-10R, interleukin-12R, interleukin-13Ralpha1, interleukin-13Ralpha2, interleukin-15R, interleukin-21Ralpha), chemokines, cell death-inducing signal molecules (e.g., B7-H1, DR6 (Death receptor 6), PD-1 (Programmed death-1), TRAIL R1), costimulating molecules (e.g., B7-1, B7-2, B7-H2, ICOS (inducible co-stimulator)), growth factors (e.g., ErbB2, ErbB3, ErbB4, HGFR), differentiation-inducing factors (e.g., B7-H3), activating factors (e.g., NKG2D), signal transfer molecules (e.g., gp130), BCMA, and TACI.

The abbreviation "MMAE" refers to monomethyl auristatin E.

The abbreviation "MMAF" refers to dovaline-valine-dolaisoleuine-dolaproine-phenylatanine, also referred to monomethyl auristatin F.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

Antibodies may be conjugated with any label moiety which can be covalently attached to the antibody via a cysteine thiol. For diagnostic applications, the antibody will typically be labeled with a detectable moiety.

The "drug" or "drug moiety" can be any cytotoxic, cytostatic or immunomodulatory (e.g., immunosuppressive) drug. In many instances, the drugs are conjugated to the antibody via a linker. For examples, linkers are described in U.S. Pat. Nos. 7,754,681; 7,375,078; 7,829,531; 7,659,241; 7,851,437; 7,829,531; 7,659,241; 7,498,298; 7,994,135; 7,964,567 and 7,964,567; each of which is incorporated herein by reference in its entirety and for all purposes. In one aspect, the linker is valine-citrulline ("Val-Cit" or "vc"). In another aspect, the linker is maleimidocaproyl ("mc").

II. Methods

Reference will now be made in detail to certain embodiments. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is not limited to the methods and materials described.

In some embodiments, the present invention provides methods for detecting a mass of a protein agent conjugate compound. In certain embodiments, the methods include the following steps: (a) providing a non covalently associated and non denature protein agent conjugate compound in a volatile salt and free of a non-volatile salt; (b) introducing the protein agent conjugate compound into a mass spectrometer; and (c) directly establishing the mass of the protein agent conjugate compound by mass spectrometry.

In some embodiments, the present invention provides methods for detecting a mass of a non covalently associated protein agent conjugate compound. In certain embodiments, the methods include the following steps: (a) providing a non denatured protein agent conjugate compound in a volatile salt and free of a non-volatile salt; (b) introducing the protein agent conjugate compound into a mass spectrometer; and (c) directly establishing the mass of the protein agent conjugate compound by mass spectrometry.

In some of the methods described herein, the methods further include applying a separation media under non denaturing conditions for the protein agent conjugate compound to effect separation of the protein agent conjugate compound from a matrix, whereby the protein agent conjugate compound is substantially non-denatured. In other embodiments, the present invention provides methods that include the step of introducing a separation media under non denaturing conditions for the protein agent conjugate compound to effect separation of the protein agent conjugate compound from a matrix, whereby the protein agent conjugate compound is substantially non-denatured.

In some embodiments of the methods described herein, the method includes eluting from the separation media the non denatured protein agent conjugate compound. In certain embodiments, the non denaturing conditions include a mass spectrometry compatible volatile SEC buffer. In some further embodiments, the volatile salt includes ammonium formate, ammonium acetate, or in ammonium carbonate. In certain embodiments, the volatile salt is ammonium formate. In certain other embodiments, the volatile salt is ammonium acetate. In other embodiments, the volatile salt is ammonium carbonate. In certain other embodiments, the volatile salt is a mixture of the volatile salts set forth herein.

In some embodiments, the present invention provides methods, described herein, wherein the matrix includes a non-volatile salt, a surfactant, or a buffer.

In further embodiments of the methods set forth herein, the present invention provides methods that include quantitating the relative distribution of protein agent conjugate compounds by deconvoluted ion intensity. In some of these embodiments, the present invention provides methods that include quantitating the relative distribution of protein agent conjugate compounds. In some of these embodiments, the present invention provides methods that include deconvoluting the ion intensity of an assay described herein in order to quantitate the relative distribution of the protein agent conjugate compounds.

In further embodiments of the methods set forth herein, the present invention provides that the protein agent conjugate compound includes an antibody drug conjugate.

In further embodiments of the methods set forth herein, the present invention provides that the matrix includes a formulation. In certain embodiments, the matrix is a formulation.

In further embodiments of the methods set forth herein, the present invention provides that the separation media includes size exclusion chromatography (SEC). In certain embodiments, the separation media is size exclusion chromatography (SEC). In some methods described herein, the methods include the step of separating the protein agent conjugates, set forth herein, by size exclusion chromatography.

In further embodiments of the methods set forth herein, the present invention provides the agent includes a drug, a toxin, or a label. In some embodiments of the present invention, the agent is a drug. In some other embodiments of the present invention, the agent is a toxin. In some other embodiments of the present invention, the agent is a label. In certain embodiments, the agent is a combination of any agents set forth herein.

In further embodiments of the methods set forth herein, the present invention provides that the SEC includes a silica, polystyrene-divinylbenzene or polyhydroxyethyl-aspartamide column. In some embodiments, the SEC includes a silica column. In some other embodiments, the SEC includes a polystyrene-divinylbenzene column. In some other embodiments, the SEC includes a polyhydroxyethyl-aspartamide column.

In further embodiments of the methods set forth herein, the present invention provides that the non denaturing conditions include a temperature of 50° C. In certain embodiments, the temperature of the non denaturing conditions is not greater than 50° C. In some embodiments, the temperature of the non denaturing conditions is room temperature. Room temperature includes, but is not limited to, temperatures of 20-24° C.

In further embodiments of the methods set forth herein, the present invention provides that the mass spectrometry is conducted on a ESI-MS. In other embodiments, the present invention provides that the mass spectrometry is conducted on a mass spectrometer that is attached to another device such as a chromatograph or spray nozzle for delivering the sample to be analyzed in the MS.

In further embodiments of the methods set forth herein, the present invention provides that the concentration of the volatile salt is 50 to 400 mM. In some embodiments, the concentration of the volatile salt is 50 mM. In some embodiments, the concentration of the volatile salt is 400 mM. In some embodiments, the concentration of the volatile salt is 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 mM. In some embodiments, the concentration of the volatile salt is about 50 to about 400 mM. In this context, about refers to a value which is within 10% of the value modified by the word about. For example, about 50 mM includes 45, 46, 47, 48, 49, 50, 51, 52, 53, 54, and 55 mM. For example, about 400 mM includes 360, 370, 380, 390, 400, 410, 420, 430, and 440 mM. In some embodiments, the concentration of the volatile salt is about 50 to about 300 mM. In some embodiments, the concentration of the volatile salt is about 50 to about 200 mM. In some embodiments, the concentration of the volatile salt is about 50 to about 100 mM. In some embodiments, the concentration of the volatile salt is about 100 to about 400 mM. In some embodiments, the concentration of the volatile salt is about 200 to about 400 mM. In some embodiments, the concentration of the volatile salt is about 300 to about 400 mM. In some embodiments, the concentration of the volatile salt is about 50 to about 100 mM. In some embodiments, the concentration of the volatile salt is about 50 to about 200 mM. In some embodiments, the concentration of the volatile salt is about 50 to about 300 mM. In some embodiments, the concentration of the volatile salt is about 50 to about 350 mM.

In further embodiments of the methods set forth herein, the eluted protein agent conjugate compound is immediately introduced into the mass spectrometer.

In some embodiments of the methods set forth herein, the eluted protein agent conjugate compound is continuously introduced into the mass spectrometer. In certain embodiments, the separation media is a HIC column run under non denaturing conditions. In other embodiments, the SEC is a polyhydroxyethyl-A column.

In some further embodiments of the methods set forth herein, the SEC column size is 0.1 to 7.8 mm inner diameter and 100 to 300 mm length.

In further embodiments of the methods set forth herein, the methods include the step of treating the protein agent conjugate compound with a deglycosylating reagent. In certain embodiments, the deglycosylating reagent is PNGaseF. In other embodiments, the deglycosylating agent includes an exoglycosidase enzymatic treatment, an endoglycosidase treatment or an enzymatic treatment that cleaves between the 1st and 2nd N-acetylglucosamine residues on N-glycans.

In some of the embodiments described herein, the exoglycosidase enzymatic treatment includes sialidase or beta-galactosidase.

In further embodiments of the methods set forth herein, the enzymatic treatment that cleaves between the 1st and 2nd N-acetylglucosamine residues on N-glycans includes Endo-F1, F2 or F3.

In some further embodiments of the methods set forth herein, the pH of the volatile salt is 5.5 to 7.0. In other embodiments, the methods described herein include the step wherein the pH of the volatile salt is 5.5, 5.6, 5.7, 5.8, 5.9, 6.0, 6.1, 6.2, 6.3, 6.4, 6.5, 6.6, 6.7, 6.8, 6.9, or 7.0. In some embodiments of the methods set forth herein, the pH of the volatile salt is 6,0, in some embodiments of the methods set forth herein, the pH of the volatile salt is 6.5. In some embodiments of the methods set forth herein, the pH of the volatile salt is 7.0.

In further embodiments of the methods set forth herein, the methods include quantitating the non denatured protein agent conjugate compound by mass spectrometry.

In some embodiments of the methods set forth herein, the non denatured protein agent conjugate compound includes a heavy chain or light chain antibody fragment. In some of these embodiments, the heavy chain or light chain antibody fragment further includes one or more drugs.

In further embodiments of the methods set forth herein, the antibody of the antibody dug conjugate is an antibody fragment.

In further embodiments of the methods set forth herein, the antibody fragment is selected from a Fab, Fab', F(ab')$_2$, F$_v$ fragment, diabody, linear antibody, or single-chain antibody molecule. In some of the embodiments described herein, the antibody is selected from the group consisting of an anti-CD30, anti-CD40, anti-CD19, anti-CD33 or anti-CD70 antibody. In other embodiments, the antibody of the antibody dug conjugate is a humanized antibody. In some embodiments, the antibody of the antibody dug conjugate includes a humanized antibody In further embodiments of the methods set forth herein, the drug is a maytansinoid. In some other embodiments, the drug is an auristatin. In certain embodiments, the drug is MMAE. In some embodiments, the drug is MMAF.

In further embodiments of the methods set forth herein, the mass of the protein agent conjugate compound is measured within 7.5 Da. In other embodiments, the mass of the protein agent conjugate compound is measured within 25 Da. In certain embodiments, the mass of the protein agent conjugate compound is measured within 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, 20.0, 20.1, 20.2, 20.3, 20.4, 20.5, 20.6, 20.7, 20.8, 20.9, 21.0, 21.1, 21.2, 21.3, 21.4, 21.5, 21.6, 21.7, 21.8, 21.9, 22.0, 22.1, 22.2, 22.3, 22.4, 22.5, 22.6, 22.7, 22.8, 22.9, 23.0, 23.1, 2, 23.3, 23.4, 23.5, 23.6, 23.7, 23.8, 23.9, 24.0, 24.1, 24.2, 24.3, 24.4, 24.5, 24.6, 24.7, 24.8, 24.9, 25.0, 25.1, 25.2, 25.3, 25.4, 25.5, 25.6, 25.7, 25.8, or 25.9 Da.

In further embodiments of the methods set forth herein, the mass of the protein agent conjugate compound is measured within 8.0 Da. In further embodiments of the methods set forth herein, the mass of the protein agent conjugate compound is measured within 9.0 Da. In further embodiments of the methods set forth herein, the mass of the protein agent conjugate compound is measured within 10.0 Da. In further embodiments of the methods set forth herein, the mass of the protein agent conjugate compound is measured within 11.0 Da. In further embodiments of the methods set forth herein, the mass of the protein agent conjugate compound is measured within 12.0 Da. In further embodiments of the methods set forth herein, the mass of the protein agent conjugate compound is measured within 13.0 Da. In further embodiments of the methods set forth herein, the mass of the protein agent conjugate compound is measured within 14.0 Da. In further embodiments of the methods set forth herein, the mass of the protein agent conjugate compound is measured within 15.0 Da. In further embodiments of the methods set forth herein, the mass of the protein agent conjugate compound is measured within 16.0 Da. In further embodiments of the methods set forth herein, the mass of the protein agent conjugate compound is measured within 17.0 Da. In further embodiments of the methods set forth herein, the mass of the protein agent conjugate compound is measured within 18.0 Da. In further embodiments of the methods set forth herein, the mass of the protein agent conjugate compound is measured within 19.0 Da. In further embodiments of the methods set forth herein, the mass of the protein agent conjugate compound is measured within 20.0 Da. In further embodiments of the methods set forth herein, the mass of the protein agent conjugate compound is measured within 21.0 Da. In further embodiments of the methods set forth herein, the mass of the protein agent conjugate compound is measured within 22.0 Da. In further embodiments of the methods set forth herein, the mass of the protein agent conjugate compound is measured within 23.0 Da. In further embodiments of the methods set forth herein, the mass of the protein agent conjugate compound is measured within 24.0 Da. In further embodiments of the methods set forth herein, the mass of the protein agent conjugate compound is measured within 25.0 Da.

In further embodiments of the methods set forth herein, the mass of the protein agent conjugate compound is measured within 100 ppm of the theoretical value. In other embodiments, the mass of the protein agent conjugate compound is measured within 80, 90, 100, 110, 120, or 130 ppm of the theoretical value.

The present invention sets forth methods for assaying the native intact mass of protein agent conjugates. The present invention also sets forth methods fur determining the native intact mass of protein agent conjugates.

The present invention sets forth a method for detecting the mass of a non covalently associated protein agent conjugate compound by providing a non denatured protein agent conjugate compound in a volatile salt and free of non-volatile salts; introducing the protein agent conjugate compound into a mass spectrometer; and directly establishing the mass of the protein agent conjugate compound by mass spectrometry.

The present invention provides methods wherein a protein agent conjugate is introduced into a mass spectrometer. In further of these embodiments, the mass of the intact protein agent conjugate compound is directly measured. In one of these embodiment, the protein agent conjugate compound is non denatured and in ammonium formate. In some of these embodiments, the protein agent conjugate compound is non denatured and in ammonium acetate. In other of these embodiments, the protein agent conjugate compound is non denatured and in ammonium carbonate. In some of these embodiments, the protein agent conjugate compound is an antibody agent conjugate compound which is non denatured and in ammonium carbonate. In some of these embodiments, the protein agent conjugate compound is an antibody agent conjugate compound which is non denatured and in ammonium formate. In some of these embodiments, the protein agent conjugate compound is an antibody agent conjugate compound which is non denatured and in ammonium acetate.

The present invention provides methods wherein a protein agent conjugate is introduced into a mass spectrometer. In further of these embodiments, the mass of the intact protein agent conjugate compound is directly measured. In some other of these embodiments, the protein agent conjugate compound is a fragment of an antibody agent conjugate compound, which is non denatured and in ammonium carbonate. In some of these embodiments, the protein agent conjugate compound is a fragment of an antibody agent conjugate compound which is non denatured and in ammonium formate. In some of these embodiments, the protein agent conjugate compound is a fragment of an antibody agent conjugate compound which is non denatured and in ammonium acetate.

The present invention provides methods wherein a protein agent conjugate is introduced into a mass spectrometer. In further of these embodiments, the mass of the intact protein agent conjugate compound is directly measured. In some of these embodiments, the protein agent conjugate compound is non denatured. In some of these embodiments, the protein agent conjugate is in ammonium formate and the agent is a drug. In some of these embodiments, the protein agent conjugate is in ammonium acetate and the agent is a drug. In some of these embodiments, the protein agent conjugate is in ammonium carbonate and the agent is a drug. In any of these embodiments, the drug includes MMAE or MMAF.

In related embodiments, the methods described herein provide that the protein agent conjugate compound is an antibody agent conjugate compound which is non denatured. In some of these embodiments, the protein agent conjugate is in ammonium carbonate and the agent is a drug. In some of these embodiments, the protein agent conjugate is in ammonium formate and the agent is a drug. In some of these embodiments, the protein agent conjugate is in ammonium acetate and the agent is a drug. In any of these embodiments, the present invention provides methods wherein the drug includes, but is not limited to, MMAE or MMAF. In any of these embodiments, the present invention provides methods wherein the drug includes MMAE. In any of these embodiments, the present invention provides methods wherein the drug is MMAF.

The present invention provides methods wherein a protein agent conjugate is introduced into a mass spectrometer. In further of these embodiments, the mass of the intact protein agent conjugate compound is directly measured. In some of these embodiments, the protein agent conjugate compound is non denatured. In some other embodiments, the protein agent conjugate is in ammonium formate and the agent is a toxin. In some other embodiments, the protein agent conjugate is in ammonium carbonate and the agent is a toxin. In some other embodiments, the protein agent conjugate is in ammonium acetate and the agent is a toxin. In any of these embodiments, the present invention provides methods wherein the agent is a toxin. In any of these embodiments, the present invention provides methods wherein the concentration of the salt is optionally between 50 and 400 mM. In any of these embodiments, the present invention provides methods wherein the agent is a drug.

The present invention provides methods wherein a protein agent conjugate is introduced into a mass spectrometer. In further of these embodiments, the mass of the intact protein agent conjugate compound is directly measured. In some of these embodiments, the protein agent conjugate compound is an antibody agent conjugate compound which is non denatured. In any of these embodiments, the present invention provides methods wherein the concentration of the salt is between 50 and 400 mM. In some of these embodiments, the agent is a drug. In some of these embodiments, the protein agent conjugate is in ammonium carbonate, ammonium acetate, or in ammonium formate.

In any of the embodiments set forth herein, the methods may include the step wherein the conjugate compound is introduced into a mass spectrometer, and the mass of the intact antibody agent conjugate compound is directly measured.

The present invention provides methods wherein a protein agent conjugate is introduced into a mass spectrometer. In further of these embodiments, the mass of the intact protein agent conjugate compound is directly measured. In some embodiments, the protein agent conjugate compound is an antibody agent conjugate compound which is non denatured. In related embodiments, the protein agent conjugate is in ammonium acetate, ammonium carbonate, or in ammonium formate. In some embodiments, the concentration of the salt is between 50 and 400 mM. In some embodiments, the concentration of the salt is 200 mM. In other related embodiments, the agent is a drug. In other embodiments, the buffer's pH is between 5.0 and 7.0. In any of these embodiments, the present invention provides methods wherein the agent may be a drug.

In another aspect of the methods described herein, the protein agent conjugate compound is an antibody agent conjugate compound which is non denatured and in ammonium formate; the concentration of the salt is 200 mM; the agent is a drug; and the buffer's pH is between 5.0 and 7.0. In some of these embodiments, the protein agent conjugate is in ammonium carbonate, ammonium acetate, or in ammonium formate.

In another aspect of the present invention, the protein agent conjugate compound is an antibody agent conjugate compound which is non denatured and in ammonium acetate. In some embodiments, the concentration of the salt is 200 mM; the buffer's pH is between 5.0 and 7.0; and the agent is a drug.

In another aspect of the methods herein, the protein agent conjugate compound is an antibody agent conjugate compound which is non denatured; the concentration of the salt is 200 mM; the agent is a drug; and the buffer's pH is 6.5. In some of these embodiments, the protein agent conjugate is in ammonium carbonate, ammonium acetate, or in ammonium formate. In some of these embodiments, the agent includes a drug, wherein the drug is a drug described herein.

In one aspect of the present invention, the protein agent conjugate compound is non denatured, a separation media under non denaturing conditions for the protein agent conjugate compound in a matrix is applied to effect separation of the protein agent conjugate compound from the matrix. In some embodiments, the protein agent conjugate compound is substantially non-denatured, the conjugate is introduced into a mass spectrometer, and the mass of the intact protein agent conjugate compound is directly measured. In some of these embodiments, the protein agent conjugate is in ammonium carbonate, ammonium acetate, or in ammonium formate.

The present invention provides methods wherein a protein agent conjugate is introduced into a mass spectrometer. In further of these embodiments, the mass of the intact protein agent conjugate compound is directly measured. In another aspect of the methods set forth herein, the protein agent conjugate compound is non denatured, and a separation media under non denaturing conditions for the protein agent conjugate compound in a matrix is applied to effect separation of the protein agent conjugate compound from the matrix, whereby the protein agent conjugate compound is substantially non-denatured. In some of these embodiments, the protein agent conjugate compound is in ammonium formate. In some of these embodiments, the protein agent conjugate compound is in ammonium carbonate. In some of these embodiments, the protein agent conjugate compound is in ammonium acetate. In related embodiments, a separation media under non denaturing conditions for the protein agent conjugate a separation media under non denaturing conditions for the protein agent conjugate compound in a matrix is applied to effect separation of the protein agent conjugate compound from the matrix. In related embodiments, the separation media is SEC.

In any of the above methods, the methods may include that the protein agent conjugate compound is non denatured, a separation media under non denaturing conditions for the protein agent conjugate compound in a matrix is applied to effect separation of the protein agent conjugate compound from the matrix, whereby the protein agent conjugate compound is substantially non-denatured, and the separation media is HIC under non denaturing conditions. In related embodiments, the protein agent conjugate is in ammonium carbonate. In related embodiments, the protein agent conjugate is in ammonium acetate. In related embodiments, the protein agent conjugate is in ammonium formate.

In any of the above methods, the methods may include that the protein agent conjugate compound is non denatured, a separation media under non denaturing conditions for the protein agent conjugate compound in a matrix is applied to effect separation of the protein agent conjugate compound from the matrix, whereby the protein agent conjugate compound is substantially non-denatured, and the separation media is HIC under non denaturing conditions. In related embodiments, the protein agent conjugate is in ammonium carbonate, in ammonium formate, or in ammonium acetate. In any of the methods described herein, the separation media may include SEC.

In another aspect of the above methods, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is SEC. In related embodiments, the protein agent conjugate is in ammonium carbonate, in ammonium formate, or in ammonium acetate.

In one aspect of the methods wherein the protein conjugate is introduced into a mass spectrometer, and the mass of the intact antibody agent conjugate compound is directly measured, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is HIC under non denaturing conditions. In related embodiments, the protein agent conjugate is in ammonium carbonate, in ammonium formate, or in ammonium acetate.

In one aspect of the methods wherein the protein conjugate is introduced into a mass spectrometer, and the mass of the intact antibody agent conjugate compound is directly measured, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is HIC under non denaturing conditions. In related embodiments, the protein agent conjugate is in ammonium carbonate, in ammonium formate, or in ammonium acetate. In related embodiments, the separation media is SEC and the mass spectrometer is an ESI-MS.

In another aspect of the above methods, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, the conjugate is introduced into a mass spectrometer, the mass spectrometer is an ESI-MS, and the mass of the intact antibody agent conjugate compound is directly measured. In related embodiments, the protein agent conjugate is in ammonium carbonate, in ammonium formate, or in ammonium acetate.

In another aspect of the above methods, the protein agent conjugate compound is an antibody agent conjugate compound, the conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is SEC. In related embodiments, the protein agent conjugate is in ammonium carbonate, in ammonium formate, or in ammonium acetate.

In one aspect of the above methods, the protein agent conjugate compound is an antibody agent conjugate compound, the conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is HIC under non denaturing conditions, the conjugate is introduced into a mass spectrometer, and the mass spectrometer is an ESI-MS. In related embodiments, the protein agent conjugate is in ammonium carbonate, in ammonium formate, or in ammonium acetate.

In any of the methods described herein, the methods may include the step where the mass of the intact antibody agent conjugate compound is directly measured. In any of the methods described herein, the protein agent conjugate may be present in ammonium carbonate, in ammonium formate, or in ammonium acetate.

In another aspect of the above methods, the protein agent conjugate compound is an antibody agent conjugate compound, the conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is HIC under non denaturing conditions. In related embodiments, the protein agent conjugate is in ammonium carbonate, in ammonium formate, or in ammonium acetate. In related embodiments, the mass spectrometer is an ESI-MS. In some other related embodiments, the protein agent conjugate is continuously introduced into a mass spectrometer.

In any of the methods described herein wherein the protein agent conjugate is introduced into a mass spectrometer, the conjugate may be introduced in a continuous manner. In any of the methods described herein wherein the protein agent conjugate is introduced into a mass spectrometer, the conjugate may be introduced continuously.

In another aspect of the above methods, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the mass spectrometer is an ESI-MS. In related embodiments, the protein agent conjugate is in ammonium carbonate, in ammonium formate, or in ammonium acetate.

In one aspect, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is HIC under non denaturing conditions. In related embodiments, the protein agent conjugate is in ammonium carbonate, in ammonium formate, or in ammonium acetate.

In any of the methods described herein, the mass spectrometer may include an ESI-MS.

In another aspect of the above methods, the protein agent conjugate compound is an antibody agent conjugate compound, the conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is HIC under non denaturing conditions. In related embodiments, the protein agent conjugate is in ammonium carbonate, in ammonium formate, or in ammonium acetate. In other related embodiments, the mass spectrometer is an ESI-MS.

The present invention provides methods wherein the separation media is SEC, the protein conjugate is introduced into a mass spectrometer, the mass spectrometer is an ESI-MS, and the mass of the intact antibody agent conjugate compound is directly measured and the mass of the antibody drug conjugate compound is quantitated. In another aspect, the protein agent conjugate compound is an antibody agent conjugate compound, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured. In related embodiments, the protein agent conjugate is in ammonium carbonate, in ammonium formate, or in ammonium acetate. In other related embodiments, the separation media is HIC under non denaturing conditions.

In one aspect, the protein agent conjugate compound is an antibody agent conjugate compound, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, the SEC column is silica, polystyrene-divinylbenzene or polyhydroxyethyl-aspartamide, and the antibody agent conjugate compound is introduced into a mass spectrometer, and the mass of the intact antibody agent conjugate compound is directly measured. In related embodiments, the protein agent conjugate is in ammonium carbonate, in ammonium formate, or in ammonium acetate.

In one aspect of the above methods, the protein agent conjugate compound is an antibody agent conjugate compound, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, and the separation media is SEC. In related embodiments, the SEC column is silica. In related embodiments, the protein agent conjugate is in ammonium carbonate, in ammonium formate, or in ammonium acetate. In other related embodiments, the SEC includes polystyrene-divinylbenzene In any of the methods herein wherein the antibody agent conjugate compound is introduced into a mass spectrometer, and the mass of the intact antibody agent conjugate compound is directly measured, the methods may further include that the protein agent conjugate compound is an antibody agent conjugate compound, that the protein agent conjugate compound is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is polyhydroxyethyl-aspartamide. In related embodiments, the protein agent conjugate is in ammonium carbonate, in ammonium formate, or in ammonium acetate.

In any of the methods herein wherein the antibody agent conjugate compound is introduced into a mass spectrometer, and the mass of the intact antibody agent conjugate compound is directly measured, the methods may further include the following aspects. In another aspect, the protein agent conjugate compound is an antibody agent conjugate compound, is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is polyhydroxyethyl-aspartamide. In related embodiments, the protein agent conjugate is in ammonium carbonate, in ammonium formate, or in ammonium acetate.

In related embodiments, the protein agent conjugate compound is an antibody agent conjugate compound, the protein agent conjugate is optionally deglycosylated, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is silica, polystyrene-divinylbenzene or polyhydroxyethyl-aspartamide. In related embodiments, the protein agent conjugate is in ammonium carbonate, in ammonium formate, or in ammonium acetate.

In another aspect of the methods wherein the antibody agent conjugate compound is introduced into a mass spectrometer, and the mass of the intact antibody agent conjugate compound is directly measured, the methods may include the following aspects. In another aspect, the protein agent conjugate compound is an antibody agent conjugate compound, the protein agent conjugate is deglycosylated, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is silica, polystyrene-divinylbenzene or polyhydroxyethyl.-aspartamide. In related embodiments, the protein agent conjugate compound is an antibody agent conjugate compound, is non denatured. In other related embodiments, the protein agent conjugate is in ammonium carbonate and the concentration of the ammonium carbonate is between 50 and 400 mM. In other related embodiments, the protein agent conjugate is in ammonium acetate and the concentration of the ammonium carbonate is between 50 and 400 mM. In other related embodiments, the protein agent conjugate is in ammonium formate and the concentration of the ammonium carbonate is between 50 and 400 mM.

In any of the methods described herein, the methods may provide that protein agent conjugate is in ammonium carbonate and the concentration of the ammonium carbonate is between 50 and 400 mM. In any of the methods described herein, the methods may provide that protein agent conjugate is in ammonium acetate and the concentration of the ammonium acetate is between 50 and 400 mM. In any of the methods described herein, the methods may provide that protein agent conjugate is in ammonium formate and the concentration of the ammonium formate is between 50 and 400 mM.

In another aspect of the methods herein wherein the antibody agent conjugate compound is introduced into a mass spectrometer, and the mass of the intact antibody agent conjugate compound is directly measured, the methods may include the following aspects. In one aspect, the separation media has non denaturing conditions for the antibody agent conjugate compound in a matrix and is applied to effect separation of the antibody agent conjugate compound from the matrix, whereby the antibody agent conjugate compound is substantially non-denatured, the separation media is SEC. In related embodiments, the SEC column is silica, polystyrene-divinylbenzene or polyhydroxyethyl-aspartamide. In any of the methods described herein, the methods may provide that protein agent conjugate is in ammonium carbonate and the concentration of the ammonium carbonate is between 50 and 400 mM. In any of the methods described herein, the methods may provide that protein agent conjugate is in ammonium acetate and the concentration of the ammonium acetate is between 50 and 400 mM. In any of the methods described herein, the methods may provide that protein agent conjugate is in ammonium formate and the concentration of the ammonium formate is between 50 and 400 mM.

In related embodiments, the present invention provides methods where the protein agent conjugate compound is an antibody agent conjugate compound, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is silica, polystyrene-divinylbenzene or polyhydroxyethyl-aspartamide. In related embodiments, the protein agent conjugate is in ammonium formate at a concentration of between 50 and 400 mM and the pH is 6.5, the protein agent conjugate is in ammonium carbonate at a concentration of between 50 and 400 mM and the pH is 6.5, or the protein agent conjugate is in ammonium acetate at a concentration of between 50 and 400 mM and the pH is 6.5. In other related embodiments, the protein agent conjugate is in ammonium formate at a concentration of 250 mM and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In any of the methods described herein, the present invention provides that the methods may optionally include that the protein agent conjugate is in ammonium formate at a concentration of 50 mM and the pH is 6.5, the protein agent conjugate is in ammonium carbonate at a concentration of 50 mM and the pH is 6.5, or the protein agent conjugate is in ammonium acetate at a concentration of 50 mM and the pH is 6.5.

In any of the methods described herein, the present invention provides that the methods may optionally include that the protein agent conjugate is in ammonium formate at a concentration of 150 mM and the pH is 6.5, the protein agent conjugate is in ammonium carbonate at a concentration of 150 mM and the pH is 6.5, or the protein agent conjugate is in ammonium acetate at a concentration of 150 mM and the pH is 6.5.

In any of the methods described herein, the present invention provides that the methods may optionally include that the protein agent conjugate is in ammonium formate at a concentration of 250 mM and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In any of the methods described herein, the present invention provides that the methods may optionally include that the protein agent conjugate is in ammonium formate at a concentration of 400 mM and the pH is 6.5, the protein agent conjugate is in ammonium carbonate at a concentration of 400 mM and the pH is 6.5, or the protein agent conjugate is in ammonium acetate at a concentration of 400 mM and the pH is 6.5.

In another aspect of the methods herein wherein the antibody agent conjugate compound is introduced into a mass spectrometer, the mass of the intact antibody agent conjugate compound is directly measured, and the mass spectrometer is an ESI-MS, the methods may include the following aspects. In one aspect, the protein agent conjugate compound is an antibody agent conjugate compound and is non denatured. In related embodiments, the protein agent conjugate is in ammonium formate at a concentration of 250 mM and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In another aspect of the methods herein wherein the antibody agent conjugate compound is introduced into a mass spectrometer, the mass of the intact antibody agent conjugate compound is directly measured, and the mass spectrometer is an ESI-MS, the methods may include the following aspects. In one aspect, the protein agent conjugate compound is an antibody agent conjugate compound, the protein agent conjugate is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is polyhydroxyethyl-aspartamide. In related embodiments, the protein agent conjugate is in ammonium formate at a concentration of 250 mM and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In another aspect of the methods herein wherein the antibody agent conjugate compound is introduced into a mass spectrometer, the mass of the intact antibody agent conjugate compound is directly measured, and the mass spectrometer is an ESI-MS, the methods may include the following aspects. In one aspect, the protein agent conjugate compound is an antibody agent conjugate compound and is non denatured, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is polyhydroxyethyl-aspartamide. In related embodiments, the protein agent conjugate is in ammonium formate at a concentration of 250 mM and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In some methods described herein, the antibody agent conjugate compound is substantially non-denatured, the separation media is SEC, and the SEC column is polyhydroxyethyl-aspartamide. In related embodiments, the protein agent conjugate is in ammonium formate at a concentration of 250 mM and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In another aspect of the methods herein wherein the antibody agent conjugate compound is introduced into a mass spectrometer, the mass of the intact antibody agent conjugate compound is directly measured, and the mass spectrometer is an ESI-MS, the methods may include the following aspects. In one aspect of a method described herein, the protein agent conjugate compound is an antibody agent conjugate compound, the agent is a drug, a separation media under non denaturing conditions for the antibody agent conjugate compound in a matrix is applied to effect separation of the antibody agent conjugate compound from the matrix, whereby the antibody agent conjugate compound is substantially non-denatured, the separation media is SEC, and the SEC column is polyhydroxyethyl-aspartamide. In related embodiments, the protein agent conjugate is in ammonium formate at a concentration of 250 trill and the pH is 6.5, the protein agent conjugate is in ammonium carbonate at a concentration of 250 mM and the pH is 6.5, or the protein agent conjugate is in ammonium acetate at a concentration of 250 mM and the pH is 6.5.

In some embodiments, the methods described herein include the rapid determination of the intact mass of non-covalently associated protein agent conjugate compounds. In one embodiment, an antibody agent conjugate compound of heavy chains (HC) and light chains (LC) is present as a complex which results from the reduction of the antibody and subsequent conjugation of drug to interchain cysteine residues. The methods described herein may include the step of analyzing the ADC using native desalting conditions, wherein the intact-bivalent structure of the ADC is maintained. Further embodiments of the present invention include the step where the mass of the desalted ADC is subsequently determined using desolvation and ionization conditions. In some of these embodiments, the desolvation and ionization conditions are standard desolvation and ionization conditions.

The methods described herein may include analyzing cysteinyl-linked ADC's by presenting a semi-native size-exclusion chromatography (SEC) based desalting and mass measurement method. The method may also include measuring the intact mass of interchain cysteine-linked ADC's, and quantitating the relative distribution of drug-linked species by deconvoluted ion intensity. The method described herein may be adapted for high throughput mass determination of ADC's.

The method described herein may include the optional step of deglycosylating the ADC. The deglycosylation step may include using PNGase F or other compounds known to one of skill in the art. The methods described herein may include the step of eliminating glycan heterogeneity. In certain embodiments, the methods provide for an improved or enhanced or greater signal intensity for each drug loaded species. In further embodiments, the methods include the step of quantitating. The present invention provides method wherein the deglycosylation allows for better mass accuracy due to increased MS signal intensity.

In addition to optional deglycosylation, the method herein may include a separation media step. The separation media step includes various chromatographic techniques, for example SEC or HIC. In this step, the ADC is exchanged from a buffer system into a volatile salt that supports positive charging of basic amino acids for mass measurement. In some of these embodiments, non-volatile salts, surfactants, and buffers are removed from the ADC. In other embodiments, the chromatographic step is performed using SEC, under non denaturing conditions, while allowing for a buffer exchange of the ADC into a volatile salt.

The method set forth herein may include a mass spectrometry step. In certain aspects, the MS step may immediately follow from the separation media step. In other aspects, there may be intervening steps between the separation media and MS step. In yet other aspects, the MS step may be continuous following the separation media step. In the MS step, the mass of the ADC is measured. Additionally, the methods set forth herein may provide that the quantitative drug loading is determined via MS ion abundance. In one aspect, the MS is performed on a TOF-MS, a Q-TOF, FTICR, Orbitrap, or high resolution ion-trap MS. In this step, the mass is measured with a high resolution mass spectrometer and the multiple charged (m/z) data is deconvoluted to zero charge mass spectra. Individual drug loaded species are quantitated on the basis of ion intensity of the deconvoluted spectrum which is a product of the intensity of the unprocessed raw data. ESI-MS raw data from proteins typically is visualized as a series charged ions where a given single molecular species may have several ions associated with it and each related ion will differ in the number of positive charges. Deconvolution of the raw data refers to the process of determining the number of charges each ion is carrying and converting all related ions into a zero charge mass spectrum which represents the molecular weight of the species that is being analyzed. Each ion in the raw data that is related to a particular species in the deconvoluted mass spectrum has an intensity or abundance measure associated with it, and the abundance of all ions associated with a particular species thus constitutes an approximation of the abundance of that species in the sample that is analyzed. When species are quantitated, the abundance of a particular species in a sample is compared to the sum of the abundance of all related species in the sample thus giving a measure of relative molar abundance of that particular species. Quantitation in this manner assumes, in certain instances, that all species have approximately equivalent ionization efficiency.

III. Pharmacokinetics

Monitoring circulating levels of a therapeutic for pharmacokinetic (PK) determinations in a mammal, including half-life, clearance, area under the curve (AUC), and volume of distribution, is necessary to establish safety/toxicity limits and appropriate dosing regimen (Welling, P. (1997) Pharmacokinetics Processes, Mathematics, and Applications, 2nd Ed., American Chemical Society, Washington, D.C.). Bioavailability is the extent to which the administered compound reaches general circulation from the administered dose form, usually expressed as a percentage of the administered dose. The half-life of a compound is the time required for 50% of the peak plasma concentration of the compound to be removed by excretion or biotransformation (metabolism). The therapeutic index expresses the selectivity of the compound between the desired therapeutic activity and the undesired toxic side effects. The pharmacokinetic measurements from the methods of the invention elucidate the absorption, distribution, metabolism, and excretion (ADME) of antibodies and antibody-drug conjugates (ADC).

IV. Drug Loading

The average number of drugs per antibody in preparations of ADCs from conjugation reactions may be characterized by the methods of the present invention. The methods of the invention can determine the amount of bound drug per antibody (loading) of an ADC and the distribution of drug moieties on fragments such as heavy chain and light chain.

V. Administration of Antibody Drug Conjugates

The ADCs may be contacted with, or administered to, biological sources by any route appropriate to the condition to be treated. The ADC will typically be administered to a mammal parenterally, e.g. infusion, subcutaneous, intramuscular, intravenous, intradermal, intrathecal and epidural.

VI. Drugs Suitable for Use with the Methods Described Herein

Exemplary drugs for conjugation to an antibody include cytotoxic drugs or agents, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors. DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, the dolastatins, the maytansinoids, differentiation inducers, and taxols. Exemplary drug moieties include, but are not limited to: auristatins (such as MMAF and MMAE), methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, maytansinoids, caminomycin, aminopterin, tallysomycin, podophyllotoxin and podophyllotoxin derivatives such as etoposide or etoposide phosphate, vinblastine, vincristine, vindesine, taxol, taxotere, retinoic acid, butyric acid, camptothecin, calicheamicin, esperamicin, enediynes, and their derivatives and analogues.

The drug moiety of an ADC can also include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activities (Pettit et al (1998) Antimicrob. Agents Chemother. 42:2961-2965). In some embodiments, the drug is an auristatin, an anti-tubulin agent. The dolastatin or auristatin drug moiety may be attached to the antibody through the N (amino) terminus or the C (carboxyl) terminus of the peptidic drug moiety (WO 02/088172). Variants of auristatin are disclosed in U.S. Pat. No. 5,767,237 and U.S. Pat. No. 6,124,431.

MMAE and MMAF immunoconjugates, their synthesis and structure, are disclosed in U.S. Pat. Nos. 7,851,437; 7,829,531; 7,659,241; 7,498,298; 7,994,135; 7,964,567; each of which is incorporated herein by reference in its entirety and for all purposes. Auristatins include, but are not limited to, auristatin E and derivatives thereof. AFP, AEB, AEVB, MMAF, and MMAE are examples of auristatins that can be used herein.

VII. Pharmaceutical Formulations

Pharmaceutical formulations of therapeutic ADCs are typically prepared for parenteral administration, e.g. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Acceptable diluents, carriers, excipients, and stabilizers are nontoxic to biological source recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including guar gum and dextrins; sugars such as glucose, mannose, sucrose, mannitol, trehalose or sorbitol; chelating agents such as EDTA; salt-forming counter-ions such as sodium; metal complexes (e.g. Zn-protein complexes); and/or non-ionic surfactants such as TWEEN™, PLURONICS™ or polyethylene glycol (PEG).

VIII. Deglycosylation

The optional deglycosylation step is employed to reduce the heterogeneity that results from the variable extent of terminal sialic acid and galactoser residues on N-glycans. Terminal N-glycan heterogeneity can be reduced with exoglycosidase enzymatic treatment (e.g., sialidase and beta-galactosidase, respectively) or by endoglycosidase treatment with enzymes that remove the N-glycan from the occupied Asn residue (e.g., PNGase-F) or enzymes that cleave between the 1st and 2nd N-acetylglucosamine residues on N-glycans (e.g., Endo-F1, F2 or F3).

In one aspect, the simplest and most effective way to reduce heterogeneity from N-glycans is to digest with PNGase-F. The deglycosylation step is optional in that quantification is still possible with the glycans left intact. However, the MS spectrum is needlessly complicated and a high end mass spectrometer would be required for reproducible quantification.

IX. Chromatography

The removal of non-volatile salts and ionic and non-ionic surfactants from protein samples occurs before mass measurement. In one embodiment, the ADC is introduced into the mass spectrometer and is free of non-volatile salts. In another embodiment, the ADC is introduced into the mass spectrometer and is substantially free of non volatile salts. In yet another embodiment, the ADC is introduced into the mass spectrometer and is free of non-volatile salts, with the exception of surfactants, for example. Cysteine linked ADC desalting techniques must keep the native protein structure intact while also removing non-ionic salts and surfactants. The chromatographic column types which can desalt and preserve native structure in MS compatible buffer systems include size-exclusion (SE) and HIC columns. It is envisioned that columns can be used that are not labeled as SEC columns, for example HIC columns, in an SEC-like mode. The columns would be run in, for example, an isocratic ammonium acetate buffer. The column operates in such a manner as to prohibit the protein from entering into the pores of the chromatographic media while permitting the non-volatile salts to enter into the pores of the chromatographic media thus causing the protein to elute first in the conditions of the mobile and the salts to elute later. The migration of the non-volatile salts is retarded with respect to the migration of the protein.

SEC columns employ a chromatographic media which is typically composed of polystyrene-divinylbenzene or polyhydroxyethyl-aspartamide stationary phase in the form of particles ranging in size from 17 to 20 microns in diameter with pore sizes ranging from 60 to 2000 angstroms. In one aspect, the pore sizes are 60, 80, 100, 120, 150, 200, 300, 500, 1000, 2000, or 4000 A. In one aspect, any SEC column packing material may be used and column sizes may be from 0.1 to 7.8 mm inner diameter and 50 to 600 mm length. The column sizes may be 0.1, 0.15, 0.3, 0.5, 1, 2.0, 2.1, 3.0, 4.0, 4.6 or 7.8 mm. The column lengths may be 50, 100, 150, 200, 250 or 300 mm.

This class of columns removes non-volatile salts and surfactants from proteins due to the vast difference in size of one with respect to the other. Specifically, small molecule salts and surfactants interact (e.g., enter into) the pores in the chromatographic particles which causes these species to be retarded in their passage through the column white proteins of sufficient size do not interact with the porous structure of the particles and thus are eluted well before the non-volatile salts and surfactants. Another aspect of a desalting system is the choice of MS compatible SEC buffer salt and the pH and concentration of the salt. The buffer salt should be volatile so as to prevent crystallization and corrosion of the MS entrance. Commonly used volatile MS buffer salts are ammonium formate/formic acid and ammonium acetate/acetic acid (cg, of acid/base pairs). For example, the columns could be washed with ammonium acetate at pH 7 and titrated down to a 6.5 pH with acetic acid. In one aspect, the salt is ammonium acetate.

The concentration of the salts is between 50 and 400 in mM. In one aspect, the salt concentration is 200 mM. In another aspect, the salt concentration is 250 mM. The buffer's pH is between 5.0 and 7.0. In one aspect, the pH is from 5.5 to 7.0. In another aspect, the pH is 6.5. In yet another aspect, the pH is 7.0. It is understood by one of skill in the art that a range of pHs is envisioned which would result in useful mass data (for example, useful mass data may be obtained at a pH of 7.5 or 8.0).

The denaturation and the ensuing fragmentation of an ADC can be prevented if the analysis occurs in the absence of organic solvents and acidic ion-pairing reagents. In one aspect, 200 mM of ammonium acetate at pH 6.5, used in conjunction with a polyhydroxyethyl-A column provides desalting of a deglycosylated IgG1 mAb.

X. Mass Spectrometry

In a MS procedure, a sample is loaded into the MS instrument. The sample contains a protein agent conjugate compound. The sample is ionized either with acid or base for positive or negative ionization MS, respectively. The sample enters the source as a fine spray of droplets. The sample containing droplets are desolvated (evaporated) with a heated drying gas. The size of the droplets decreases to the point where the positively charged protein molecules cause the droplets to explode into smaller droplets because of electrostatic repulsions. This process repeats many times in a split second until having true gas phase protein ions which subsequently enter the mass spectrometer for mass determination. This process is typically referred to as electrospray-ionization (ESI). The mass to charge ratio (m/z) of the molecular ions is determined and this raw data is further processed (deconvoluted) by vendor specific software to yield zero charge molecular mass for the analyte of interest. MS is used to study pharmacokinetics, identify unknown protein or small molecules and characterize posttranslational modifications and degradations occurring on proteins. Typical ESI instrumentation includes water Xevo Q-TOF, Agilent 6510 Q-TOF.

Mass spectrometric data is used to confirm the primary structure of proteins. Confirmation of primary structure is obtained when the experimentally measured mass of a protein matches the theoretical mass, which is determined from the expected amino acid sequence, within a given error threshold. Intact mass measurement of recombinant mAbs can be carried out using most commercially available time of flight mass spectrometers. Typical desalting procedures using denaturing solvent systems often yield experimental mass data for mAbs that is within 50 ppm (approximately 7.5 Da) of the theoretical value. In other aspects, the mass data is within approximately 25 Da. Native desalting of mAbs and ADC's using SEC-MS in an ammonium acetate buffer system results in lower ionization efficiencies because fewer basic residues are positively charged at neutral buffer pH. Lower intensity raw data can result in greater deviation of the experimentally measured mass from the theoretical mass. Nevertheless, experimental mass data obtained on ADC's desalted using SEC-MS described herein routinely yields mass data that is within 50 ppm (approximately 7.5 Da) of the theoretical value and always less than 100 ppm. The high degree of mass accuracy indicates that the ADC is fully desalted all common salt adducts that could potentially be associated with the protein would increase the mass by at least 18 Da (the mass of an ammonium ion). Conventional approaches to measuring the mass of ADC's with noncovalently attached subunits involve desalting through offline techniques such as centrifugal filtration, single use gel permeation cartridges and dialysis followed by nanospray MS of the desalted ADC. Incomplete de-adducting of the sample is quite common using this approach and can result in mass data which deviates from the theoretical value by up to 5000 ppm.

Upon elution of the protein, for example an ADC, from the SEC column in a volatile salt, for example ammonium acetate, the protein is introduced into the mass spectrometer using commercially available analytical ESI sources capable of desolvating and ionizing proteins in buffer that is flowing between 1 and 1000 microliters/minute. Flow rates may be determined by the operator and can be dependent on column diameter. For example, a 0.1 mm column could be operated at a flow rate of 1 microliter/min and 7.8 mm could be operated at around 1000 microliters/min. This flow rate allows for much faster determination of mass. Capillary voltage, gas flow rates (desolvation and sheath) and cone voltages should be set at values which are sufficient to desolvate (e.g., evaporate the solvent) the ADC but gentle enough to minimize in-source fragmentation of the ADC into drug linked heavy and light chains. When the native-folded structure of the ADC is maintained, then the raw data is evident as a charge envelope between 4800 and 7000 m/z. If native structure is not maintained then this is evident as a significant population of ADC having a charge envelope between 2000 and 4000 m/z. The raw data from MS measurement of the ADC is converted to a zero charge mass spectrum using commercially available deconvolution software (e.g., Agilent MassHunter maximum entropy deconvolution) and the abundances of each drug linked species is quantitated by dividing the ion abundance of a particular drug linked species by the total ion abundance (summed abundance of all drug linked species). Mass measurement of intact proteins is typically carried out on time of flight and quadrupole time of flight (TOF and QTOF respectively) instruments but also may be carried out on Fourier transform ion cyclotron resonance (FT-ICR) and orbitrap mass spectrometers. In one aspect, this work could be performed on matrix assisted laser desorption ionization (MALDI) mass spectrometers and higher resolution ion-trap mass spectrometers.

In contrast to the present invention, previously each collected fraction from the chromatography step was introduced individually into the MS. By assaying the mass of each fraction's constituent compounds and conjugates, the sum of the mass of all the collected peaks was calculated to determine the overall mass. As set forth herein, the present invention provides methods analyzing the intact ADCs directly by MS.

XI. Electrospray Ionization Mass Spectrometry (ESI)

Masses of relatively high molecular weight compounds such as antibodies can be detected at mass-to-charge ratios (m/z) that are easily determined by most mass spectrometers (typical m/z ranges of up to 2000, up to 3000, up to 8000). Electrospray ionization mass spectrometry ESI-MS, in particular, is suited for charged, polar or basic compounds and for analyzing multiply charged compounds with excellent detection limits. ESI thus allows detection and characterization of large biomolecules, such as antibody-drug conjugates with molecular weight (MW) of 150,000 or higher.

XII. Systems

In some embodiments, the present invention provides a system configured to perform a method described herein. In some of these embodiments, the systems include a mass spectrometer.

In certain embodiments, the mass spectrometer is configured to perform a method described herein and includes a means for detecting a mass of a non covalently associated protein agent conjugate. In certain embodiments, the means include a mass spectrometer. In some embodiments, the systems further includes means for providing a non denatured protein agent conjugate compound in a volatile salt and free of a non-volatile salt. In further embodiments, the systems include means for introducing the protein agent conjugate compound into a mass spectrometer. In still further embodiments, the systems include means for directly establishing the mass of the protein agent conjugate compound by mass spectrometry.

XIII. Examples

The following examples exemplify the invention and are not intending to limit it.

Materials

Antibody-Drug Conjugates—Recombinant monoclonal antibodies were expressed in CHO cells and purified according to standard procedures described in Shukla, A et al, (2007) *J Chromatogr B Analyt Technol Biomed Life Sci* 848, 28-39. Conjugation of mAb cysteine residues to Val-Cit monomethyl auristatin E (vcMMAE) or maleimidocaproyl monomethyl auristatin F (mcMMAF) was carried out according to established procedures described in Sun, M. et al, (2005) *Bioconjug Chem* 16, 1282-1290. Antibodies were deglycosylated by adding 1 µl PNGase F (New England Biolabs, Ipswich, Mass.) per 100 µg of antibody or ADC and incubated at 37° C. for at least 4 hours.

EXAMPLE 1

SEC-MS Chromatography—mAbs and ADC's were separated on a polyhydroxyethyl-A column (PolyLC, Columbia, Md.) with dimensions of 2.1×200 mm and containing 5 micron particles with 300 Å pores. The column was equilibrated in either 200 mM ammonium acetate, pH 6.5-7.0 for non-denaturing mass analysis or 30% acetonitrile, 0.2% formic acid for denaturing mass analysis (control). The flow rate was maintained at 0.1 mL/min during the run and the mAb or ADC was eluted between 15 and 4.5 min. The flow and buffer composition was maintained following elution of the mAb or ADC and the total cycle time was 10 min per run.

Mass Spectrometry—Mass spectral data for mAbs and ADC's was acquired on an Agilent 6510 QTOF (Agilent, Santa Clara, Calif.) in positive ESI mode in the range 1000-8000 m/z. The drying gas temperature was 350° C. and a flow rate for the drying gas and the nebulizer gas pressure was 12 L/hr and 35 psi, respectively. The capillary, fragmentor and octupole RE voltages were set at 5000, 450 and 350, respectively. The raw data was converted to zero charge mass spectra with a maximum entropy deconvolution algorithm within the MassHunter workstation software version B.03.01.

Figure 6A:
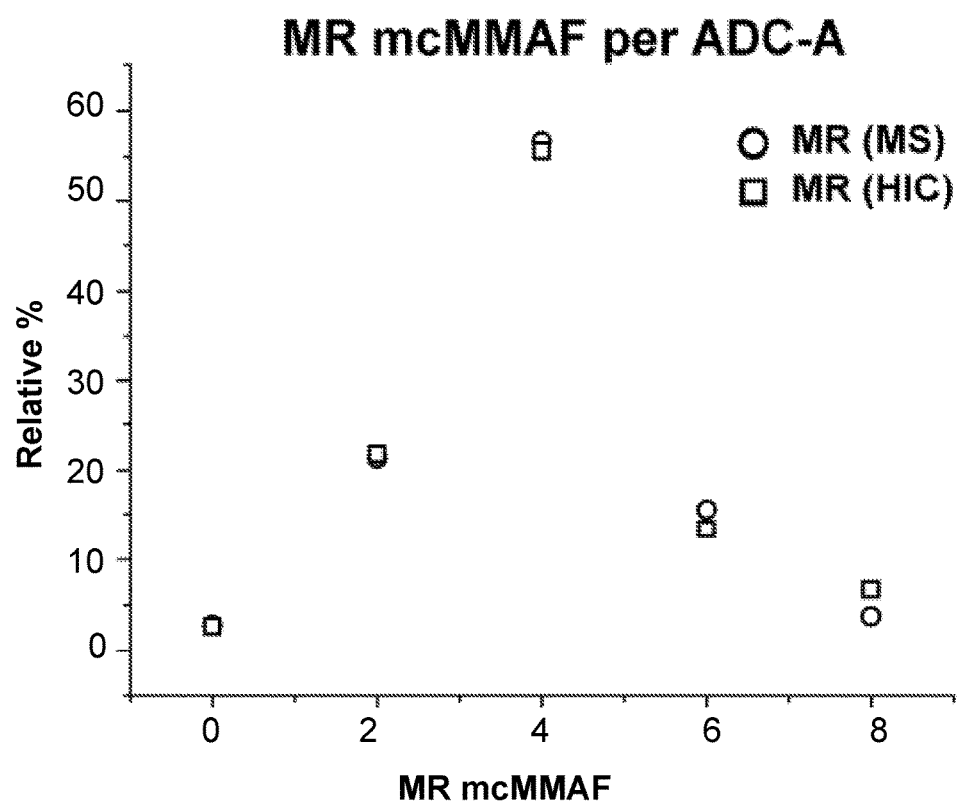
FIG. 6 shows the relative levels of the molar ratios of vcMMAF per IgG1 ADC-A (panel A) and vcMMAE per IgG1 ADC-B (panel B), as determined by MS based quantitation from the deconvoluted mass spectrums and by UV integration of the species separated by HIC.
Figure 6B:
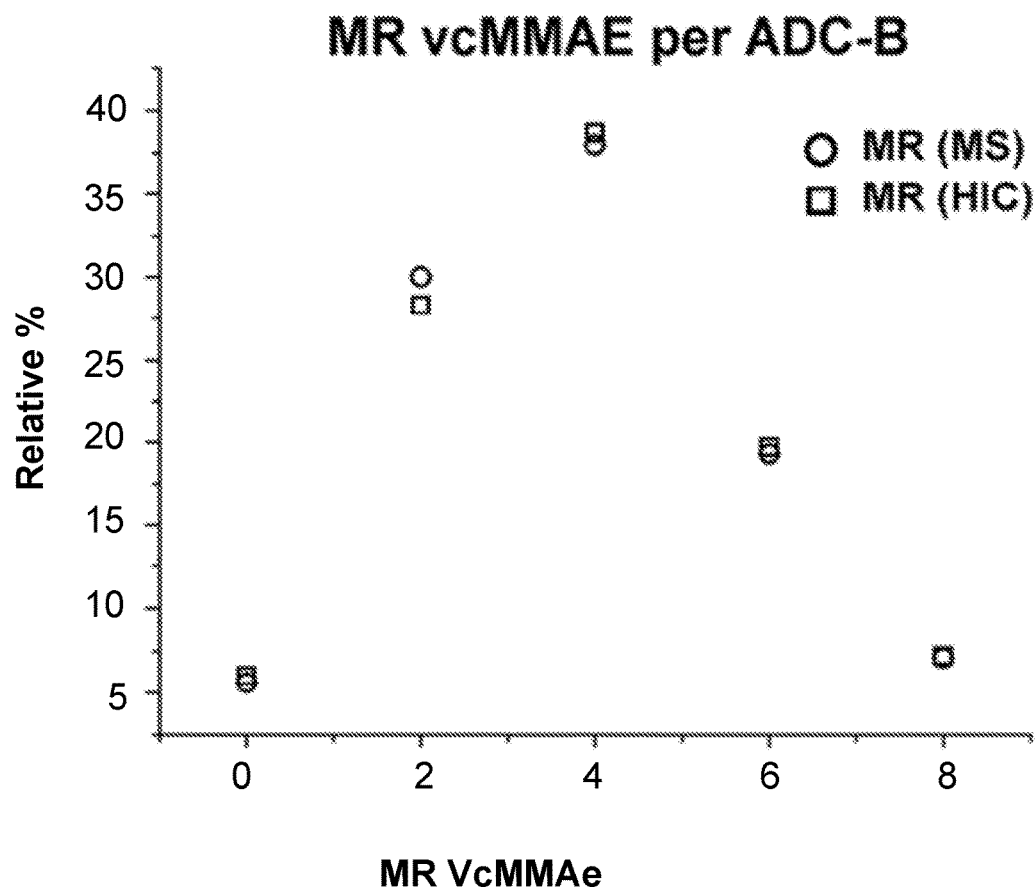

Hydrophobic Interaction Chromatography (HIC)—vcMMAE and mcMMAF ADC's were separated by HIC according to methods described in McDonagh, C. F. et al, (2006) *Protein Eng Des Sel* 19, 299-307. Quantitation of drug load species was determined by UV integration at 280 nm. In FIG. 6, the HIC data is used as a comparison of the relative percentages of ADC MR0-8 determined from the intact mass data method described herein.

In addition to FIG. 6, Table 1 shows the ion abundance area and HIC UV area values for MR of individual drug loaded species.

TABLE 1

| A | | |
|---|---|---|
| MR mcMMAF | mcMMAF IgG1 ADC-A (MS) | mcMMAF IgG1 ADC-A (HIC) |
| MR-0 | 2.8% | 2.7% |
| MR-2 | 21.3% | 21.7% |
| MR-4 | 56.6% | 55.6% |
| MR-6 | 15.5% | 13.3% |
| MR-8 | 3.8% | 6.7% |

| B | | |
|---|---|---|
| MR vcMMAE | vcMMAE IgG1 ADC-B (MS) | vcMMAE IgG1 ADC-B (HIC) |
| MR-0 | 5.6% | 6.0% |
| MR-2 | 30.0% | 28.3% |
| MR-4 | 38.0% | 38.7% |
| MR-6 | 19.3% | 19.7% |
| MR-8 | 7.1% | 7.2% |

A comparison of the raw MS data obtained from the control mAb sample desalted in the presence of 30% acetonitrile, 0.2% formic acid to the mAb/ammonium acetate desalted sample indicated that the former conditions completely denature the antibody as evidenced by the charge envelope, which was observed between 2000 and 4000 m/z, while the ammonium acetate desalt resulted in a charge envelope observed between 4800 and 6800 m/z (FIG. 2, panels A and B respectively). The ions evident between 200 and 3500 m/z in panel B which is the region in which denatured antibody would be evident are due to the presence of PNGase F which was used for deglycosylation and the non-ionic detergent Tween-80. The deconvoluted mass of the antibody determined by either method was within 10 ppm of the theoretical value (FIG. 2, panels C and D).

The mcMMAF conjugate of mAb-A described above was also analyzed using the denaturing and non-denaturing chromatographic desalting methods. Desalting of the ADC in the presence of 30% acetonitrile, 0.2% formic acid resulted in a charge envelope between 1500 and 4000 m/z (FIG. 3, panel A). The deconvoluted MS was dominated by drug-linked antibody fragments including 1LC with 1 drug, 1LC1HC with 2 drugs, 2HC with 2 drugs and 1LC2HC with 1 drug and 2LC2HC with 0 drugs (FIG. 3, panel C). The control conditions showed no evidence for the presence of intact ADC-A. The same m/z region in the ammonium acetate desalted ADC-A MS (FIG. 3, panel B) was also deconvoluted and the observed fragmentation of the ADC was much lower and only 1LC with 1 drug and 1LC1HC with 2 drugs were observed (FIG. 3, panel D). Multiply charged ions for ADC-A were only observed in the raw data for the ammonium acetate desalted sample and are indicated in the bracketed area in FIG. 3, panel B.

Figure 4:
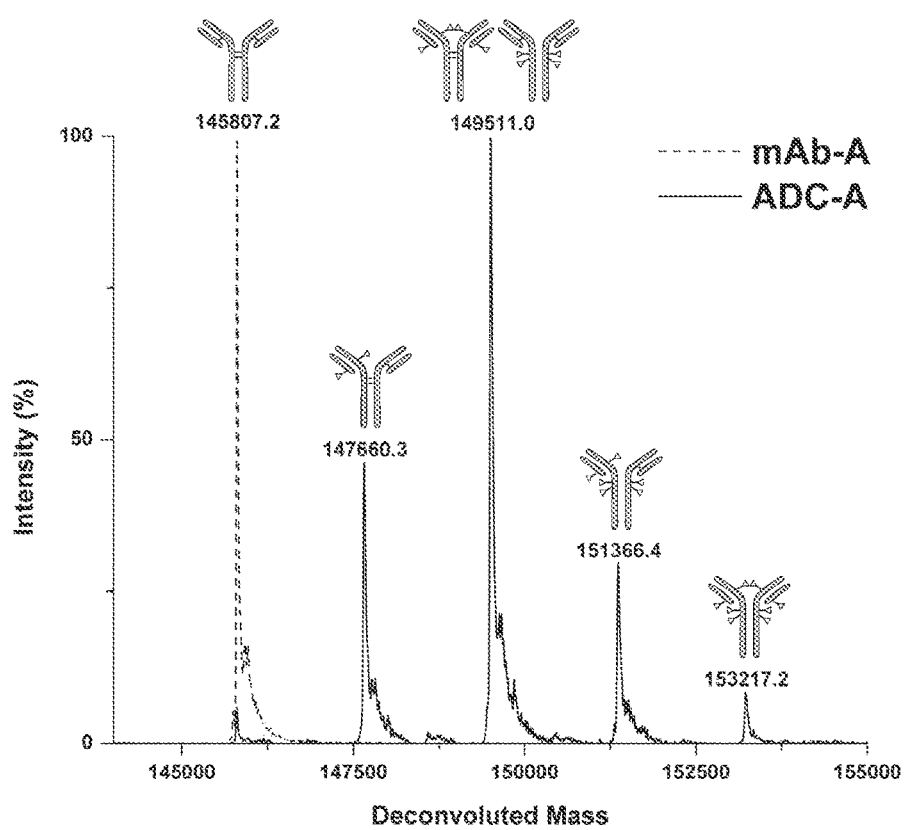
FIG. 4 shows a deconvoluted mass spectrum tier a deglycosylated maleimidocaproyl monomethyl auristatin F (mcMMAF) conjugate ADC-A and the corresponding parent material, mAB-A. Non-covalently associated ADC structures are shown above the corresponding ion in the MS.
Figure 5:
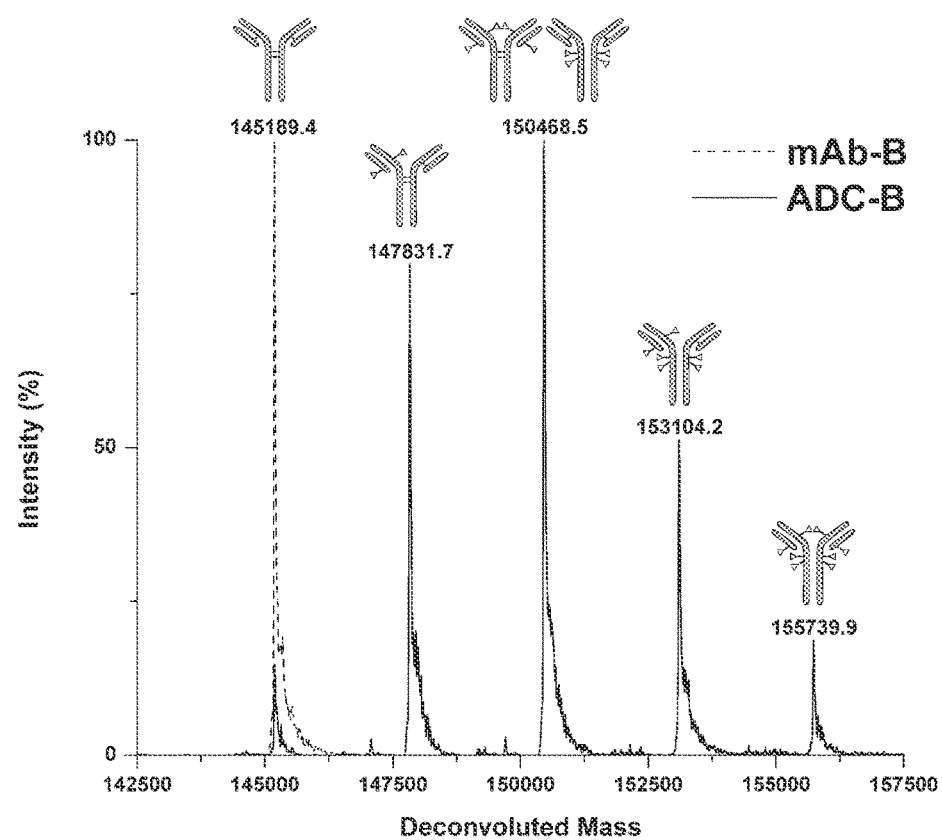
FIG. 5 shows a deconvoluted mass spectrum for a deglycosylated mc-Val-Cit-PAB monomethyl auristatin E (vcMMAE) conjugate ADC-B and the corresponding parent material, mAb-B. Non-covalently associated ADC structures are shown above the corresponding ion in the MS.

Analysis of the mcMMAF and vcMMAE ADC's by the same ammonium acetate desalting method described herein above resulted in a distribution of species with masses consistent with the mAb with incorporation of 0-8 drugs. The intact mass spectra of the mcMMAF conjugate ADC-A and the parent material (mAb-A) are shown in FIG. 4. The relative ion intensities of the individual drug loaded species were quantitated from the ion abundance associated with the deconvoluted mass spectrum. A comparison of the relative amounts of ADC MR0-8 determined from the intact mass data and from an orthogonal method, HIC, is shown in FIG. 6, panel A. Similar results were obtained for the analysis of the vcMMAE conjugate ADC-B and the parent material (mAb-B) and is shown in FIG. 5. The comparison of the relative amounts of ADC MR0-8 determined from the intact mass data and by HIC is shown in FIG. 6, panel B.

EXAMPLE 2

Size Exclusion Chromatography—ADC samples were analyzed offline by dual column SEC. Two 7.8 mm×30 cm TSK gel G3000SWXL columns packed with 5 μm particles with 250 Å pores (Tosoh, JPN) were connected in series. ADC samples were separated using a mobile phase consisting of 200 mM ammonium acetate, pH 7 at a flow rate of 0.8 ml/min. UV absorbance at 280 nm was used for detection due to interfering background absorbance of the mobile phase at lower wavelengths.

Figure 7:
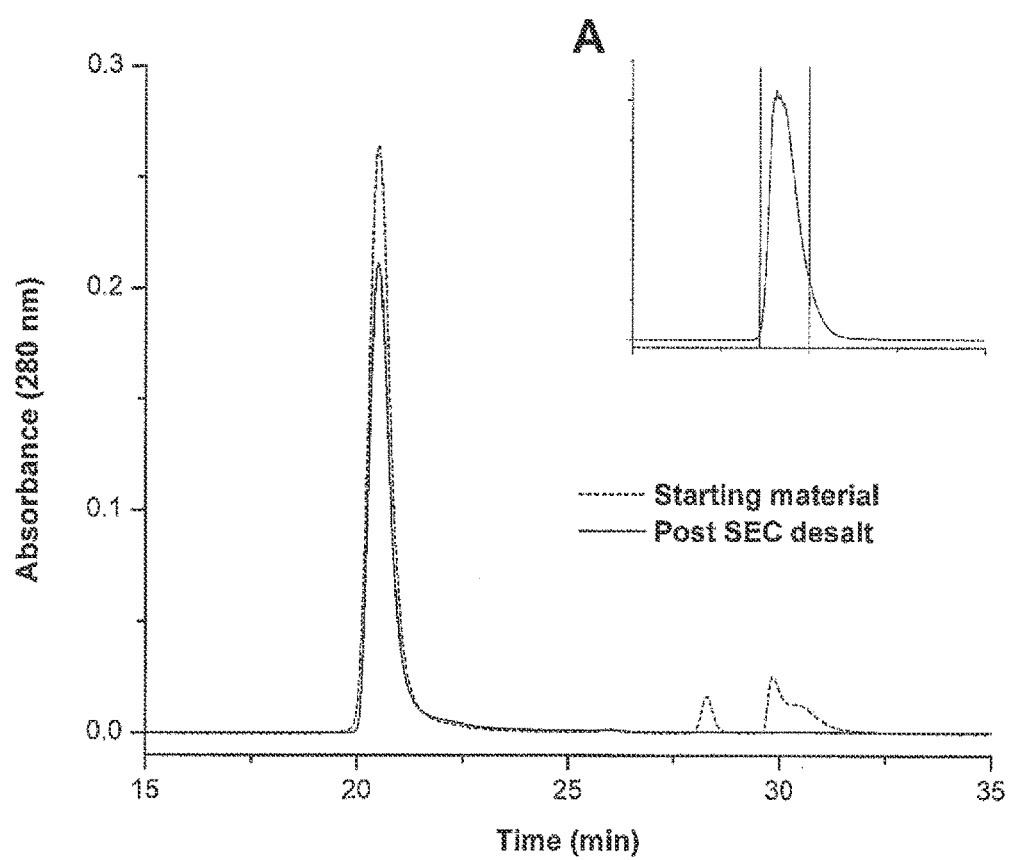
FIG. 7 shows a comparison of the chromatograms from the dual-column SEC analysis of the desalted ADC and the corresponding starting material.

The effect of the desalting method on ADC subunit dissociation was evaluated by collecting the ADC from the desalting column, and then analyzing the ADC collected from the desalting column, as well as the ADC prior to desalting, by dual-column SEC. Referring to FIG. 7, a comparison of the chromatograms from the dual-column SEC analysis of the desalted ADC and the corresponding starting material indicated that there was no increase in dissociation as a consequence of the desalting method.

EXAMPLE 3

Experimental—The PHEA SEC column was equilibrated in ammonium acetate buffer at various salt concentrations ranging from 50 mM to 400 mM. Deglycosylated ADC-B was analyzed by SEC-MS operated with mobile phase salt concentrations described above and the relative levels of MR0-MR8 were quantitated on the basis of deconvoluted ion intensity as previously described.

Results—At a salt concentration of 50 mM the levels of MR2 and MR6 appear to be over and under-represented relative to the levels observed in all other salt concentrations. This would suggest that the concentration of ammonium acetate in the SEC-MS mobile phase should be above 50 mM and that mobile phase ammonium acetate salt concentrations between 100 and 400 mM do not produce widely disparate results with respect to relative MR distribution.

Figure 8:
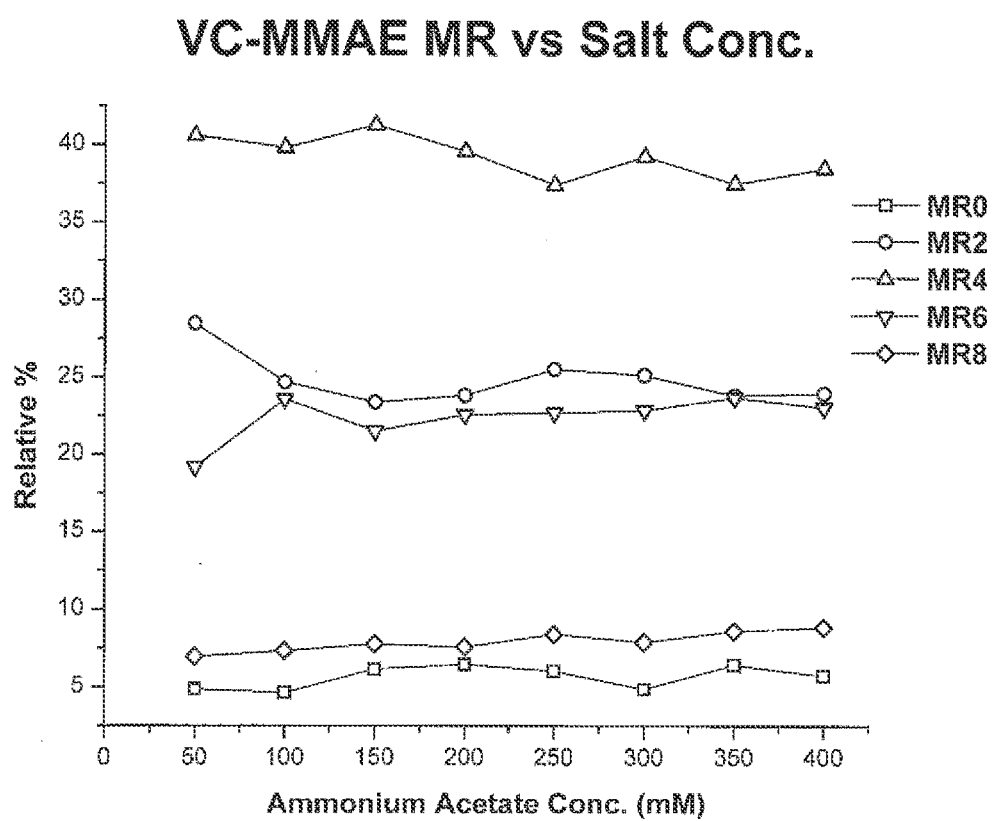
FIG. 8 shows the relative percentage of vcMMAE per salt concentration for conjugates having MR values of 0, 2, 4, 6, and 8.

FIG. 8 illustrates that changing the concentration of the ammonium acetate in the mobile phase does not impact the relative distribution of individual drug loaded forms when the salt concentration is between 100 and 400 mM.

EXAMPLE 4

Experimental—ADC-C is an IgG1 molecule conjugated to mc-MMAF. The various drug loaded forms were separated and purified by HIC chromatography (FIG. 9A). The purified fractions, as well as the ADC-C starting material (prior to HIC separation) were subsequently assessed by SEC-MS as previously described (FIG. 9B), Results—The Results from SEC-MS are consistent with orthogonal data (LCMS separation of reduce light and heavy chains) showing that peaks A-F correspond to various drug loaded forms of ADC-C (FIG. 9B). HIC peaks C and D have the same nominal mass and the mass is consistent with MR4 species. Deconvolution of the raw data in the low m/z range of 1500-4000 (FIG. 10) indicates that peak C is composed primarily of MR4 with drugs incorporated into the antibody Fab as evidenced by the observed drug-linked LC and HC dimer with 2 drugs. A similar analysis of HIC peak D indicates that it is composed primarily of MR4 with drugs incorporated into the antibody hinge as evidenced by observable covalent HC-LC with 2 drugs. Based on the information obtained from analysis of the dissociated antibody chains, it is possible to determine the identities of the MR4 positional isomers separated by HIC into peaks C and D.

Figure 9:
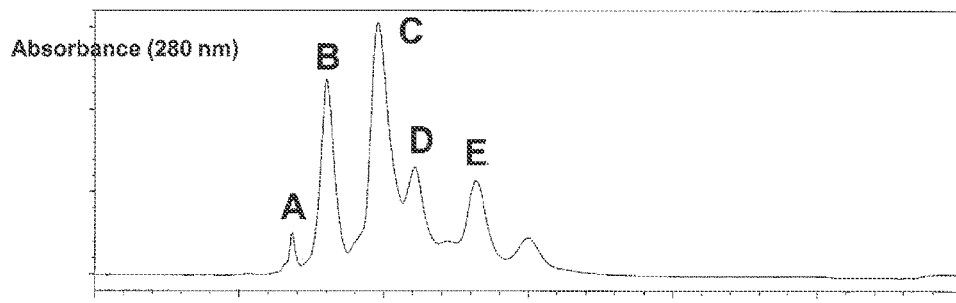
FIG. 9 the results of a characterization of separation of an mcMMAF ADC by HIC (panel A), followed by analysis of the collected fractions by SEC-MS (panel B).
Figure 9:
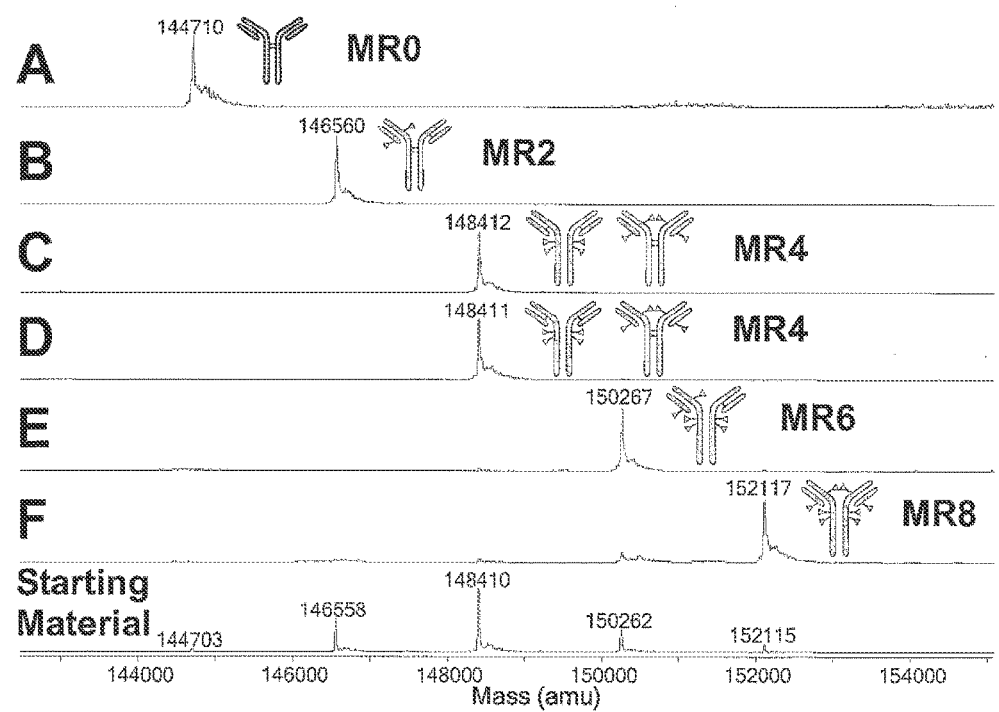
Figure 10:
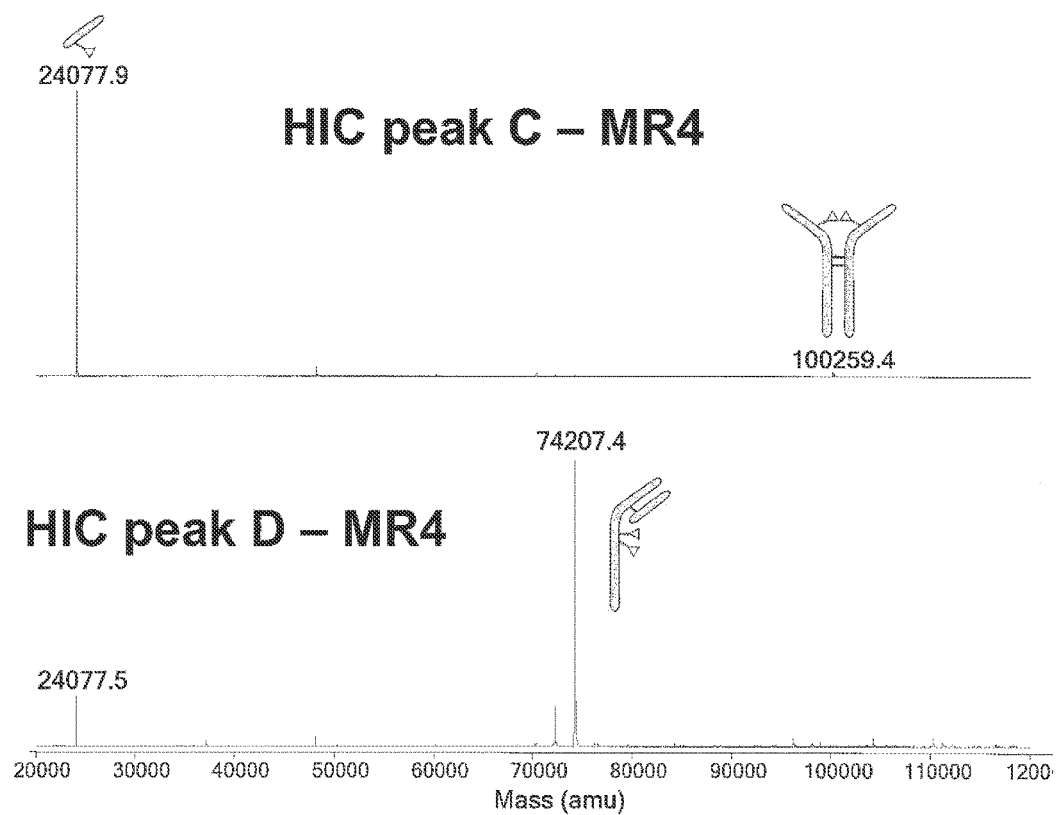
FIG. 10 shows an analysis of the individual fractions from the HIC separation shows that the position of drug linkage on ADC polypeptide chains can be assessed by the mass of the dissociated fragments using SEC-MS.

FIG. 9 shows the results of a characterization of separation of an mcMMAF ADC by HIC (panel A), followed by analysis of the collected fractions by SEC-MS (panel B). In FIG. 10, an analysis of the individual fractions from the HIC separation shows that the position of drug linkage on ADC polypeptide chains can be assessed by the mass of the dissociated fragments using SEC-MS.

EXAMPLE 5

Micro Flow SEC-MS Chromatography—ADCs were separated using a polyhydroxyethyl-A column (PolyLC, Columbia, Md.) with dimensions of 0.3×150 mm, containing 5 micron particles with 300 Å pores. The column was equilibrated with 200 mM ammonium acetate, pH 6.5-7.0 for non-denaturing mass analysis. Quantity of sample loading onto the column ranged from 2.5 μg to 50 ng. Utilizing a positive feedback microflow LC controller and ESI microflow spray device, the flow rate was maintained at 1.0 μL/min during the 25 minute isocratic 200 mM ammonium acetate gradient, with ADC elution observed between 15.5 and 19.5 minutes.

Mass Spectrometry—Mass spectral data for ADCs were acquired using an Agilent 6510 QTOF (Agilent, Santa Clara, Calif.) in positive ESI mode between 1000-8000 m/z. The drying gas temperature was 350° C., with drying and nebulizer gas pressures set to 5.0 L/hr and 15 psi, respectively. All other MS settings were identical to the analytical scale experiments except for those optimized for the micro flow/micro ESI interface including capillary voltage and skimmer voltages which were set to 3000 and 300 volts respectively. The raw data was converted to neutral mass units using a maximum entropy deconvolution algorithm within the MassHunter workstation software version B.03.01.

Figure 11:
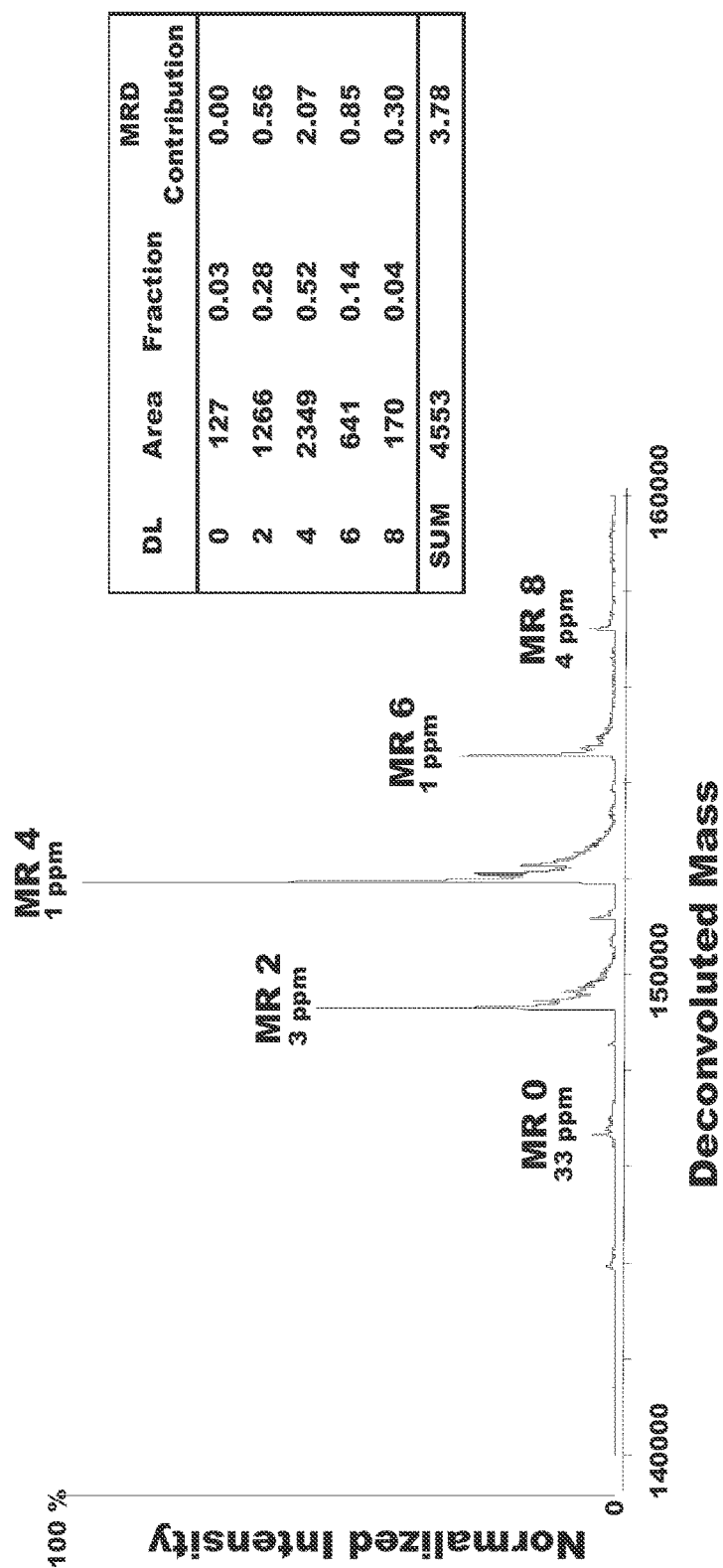
FIG. 11 shows a deconvoluted MS mass measurement for a protein agent conjugate having MR=0, 2, 4, 6, or 8.

While the lower flow rate delayed the elution time compared to the analytical method, limit of detection dramatically increased, with all four drug loaded species visible down to 50 ng of degylcosylated ADC on column. As an example, for the 500 ng ADC injection (See FIG. 11) the MRD is comparable to that observed using the analytical scale SEC method and FRC analysis. The observed mass accuracy/mass error is also substantially below the instrument specifications.

EXAMPLE 6

Plasma Stability/ADC Affinity Purification—Filtered female K2EDTA Sprague Dawley rat plasma was incubated with MabSelect to deplete endogenous IgG. ADC was spiked into the IgG deficient rat plasma at 1 mg/mL, aliquoted, and stored at 37° C. Aliquots were removed from 37° C. storage and stored at −80° C. at specified time points (0, 6 hours, 1 day, 2 days, 4 days, 7 days) until analysis. 500 μL of the 1 mg/mL ADC was then bound to MabSelect, washed in 1×PBS pH 7.4 three times, eluted in 100 μL of IgG elution buffer, and neutralized in 1 M tris pH 8 (1:10 v/v).

Micro Flow SEC-MS Chromatography—ADC's were separated using a polyhydroxyethyl-A column (PolyLC, Columbia, Md.) with dimensions of 0.3×150 mm, containing 5 micron particles with 300 Å pores. The column was equilibrated with 200 mM ammonium acetate, pH 6.5-7.0 for non-denaturing mass analysis. Utilizing a positive feedback microflow LC controller and ESI microflow spray device, the flow rate was maintained at 1.0 μL/min during the 85 minute isocratic 200 mM ammonium acetate gradient, with ADC elution observed between 15.5 and 19.5 minutes. Approximately 1 μg of ADC was injected for each acquisition.

Mass Spectrometry—Mass spectral data for the ADCs was acquired using an Agilent 6510 QTOF (Agilent, Santa Clara, Calif.) in positive ESI mode between 1000-8000 m/z. The drying gas temperature was 350° C., with drying and nebulizer gas pressures set to 5.0 L/hr and 15 psi, respectively. All other MS settings were identical to the analytical scale experiments except for those optimized for the micro flow/micro ESI interface including capillary voltage and skimmer voltages which were set to 3000 and 300 volts respectively. The raw data was converted to neutral mass units using a maximum entropy deconvolution algorithm within the MassHunter workstation software version B.03.01.

Figure 12:
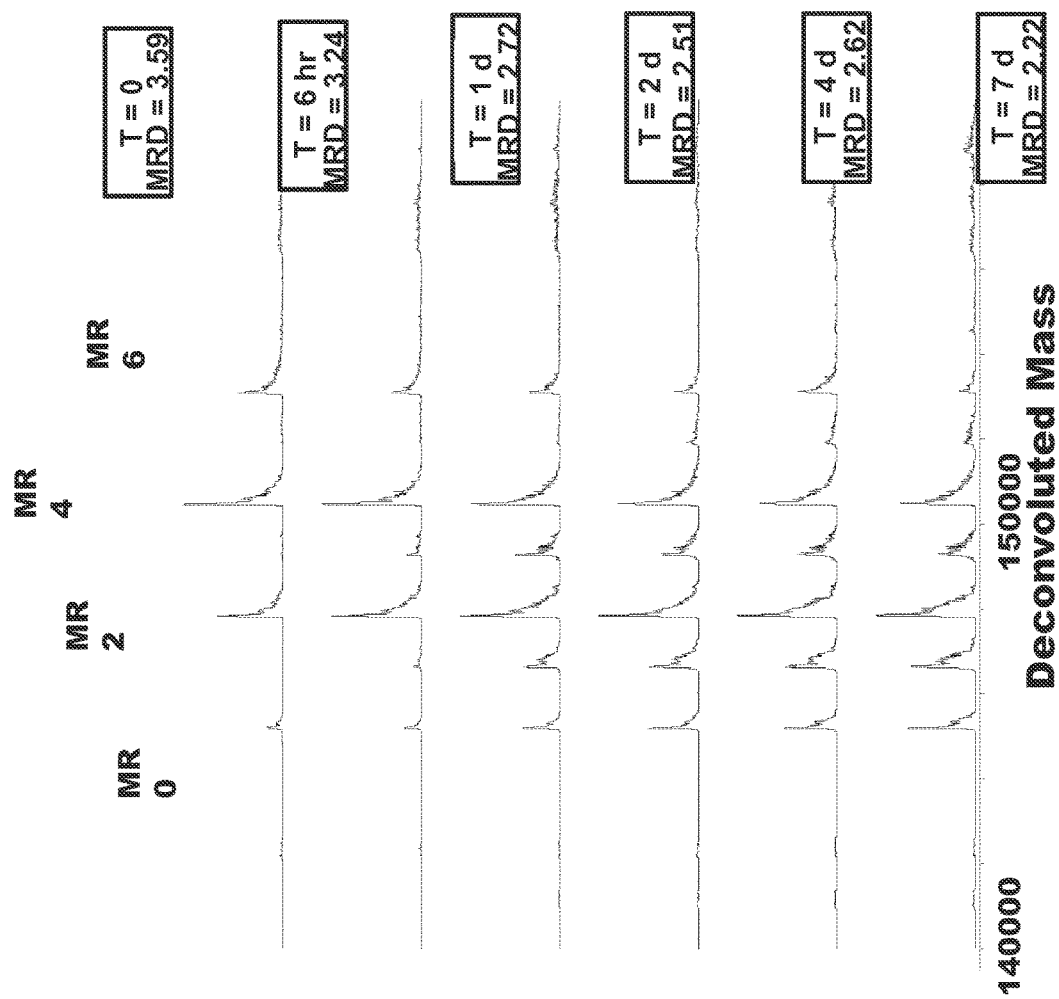
FIG. 12 shows a deconvoluted MS mass measurement for a protein agent conjugate having MR=0, 2, 4, or 6.

Column re-equilibration was extended to an hour after each ADC-purified-from-plasma injection to reduce interference from any biological contaminant. This increased signal to noise and resolution of ADC peaks. The deconvoluted data for time point zero is as expected with only even loaded species observed. As the incubation times increase, the odd loaded species appear, and increase in abundance over time (see FIG. 12). While ADC peaks at the beginning of the incubation are as expected, over time peak tailing increases. This is due to increased overall sample heterogeneity. Specifically, each drug loaded site is in competition with undergoing a reverse Michal addition or opening of the maleimide ring. This has been confirmed using reduced mass analysis. The decrease in observed MRD over time reflects the loss of drug in IgG deficient rat plasma at 37° C.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for quantitating a distribution of antibody drug conjugate compounds, in a mixture comprising:
   (a) providing the mixture in a matrix to a separation media run under non-denaturing conditions with a mobile phase to effect removal of the matrix from the mixture and produce an eluate;
   (b) introducing the eluate into a mass spectrometer;
   (c) directly establishing a mass and an ion intensity for each species of the antibody drug conjugate compounds from a deconvoluted mass spectrum; and
   (d) quantitating the distribution of the antibody drug conjugate compounds by ion intensity;

wherein:
   each species of the antibody drug conjugate compounds has from one to eight drug moieties conjugated to reduced interchain disulfides, is non-covalently associated and non-denatured, and maintains its intact-bivalent antibody structure, and the mobile phase comprises a volatile salt, is free of non-volatile salts, and is compatible for use with mass spectrometry.

2. The method of claim 1 wherein the volatile salt comprises ammonium formate, ammonium acetate, or ammonium carbonate.

3. The method of claim 1 wherein the matrix comprises a non-volatile salt, a surfactant, or a buffer.

4. The method of claim 1 wherein the matrix comprises a formulation.

5. The method of claim 1 wherein the separation media comprises size exclusion chromatography (SEC).

6. The method of claim 5 wherein the SEC comprises a silica, polystyrene-divinylbenzene or polyhydroxyethyl-aspartamide column.

7. The method of claim 1 wherein the non-denaturing conditions comprise a temperature of not greater than 50° C.

8. The method of claim 1 wherein mass spectrometry is conducted on a ESI-MS.

9. The method of claim 1 wherein the concentration of the volatile salt is 50 to 400 mM.

10. The method of claim 1 wherein the concentration of the volatile salt is 50 mM to 1 M.

11. The method of claim 1 wherein the eluate is immediately introduced into the mass spectrometer.

12. The method of claim 1 wherein the eluate is continuously introduced into the mass spectrometer.

13. The method of claim 1 wherein the separation media comprises a HIC column run under non-denaturing conditions.

14. The method of claim 6 wherein the SEC comprises a polyhydroxyethyl-A column.

15. The method of claim 6 wherein the SEC column size is 0.1 to 7.8 mm inner diameter and 100 to 300 mm length.

16. The method of claim 1 further comprising the step of treating the mixture with a deglycosylating reagent.

17. The method of claim 16 wherein the deglycosylating reagent comprises PNGaseF.

18. The method of claim 16 wherein the deglycosylating reagent comprises an exoglycosidase enzymatic treatment, an endoglycosidase treatment or an enzymatic treatment that cleaves between the $1^{st}$ and $2^{nd}$ N-acetylglucosamine residues on N-glycans.

19. The method of claim 18 wherein the exoglycosidase enzymatic treatment comprises sialidase or beta-galactosidase.

20. The method of claim 18 wherein the enzymatic treatment that cleaves between the $1^{st}$ and $2^{nd}$ N-acetylglucosamine residues on N-glycans comprises Endo-F1, F2 or F3.

21. The method of claim 1 wherein the pH of the volatile salt is 5.5 to 7.0.

22. The method of claim 1 further comprising quantitating each species of the non-covalently associated and non-denatured antibody drug conjugate compounds by mass spectrometry.

23. The method of claim 1 wherein each species of the antibody drug conjugate compounds comprises an antibody selected from the group consisting of an anti-CD30, anti-CD40, anti-CD19, anti-CD33 and anti-CD70 antibody.

24. The method of claim 1 wherein each species of the antibody drug conjugate compounds comprises a humanized antibody.

25. The method of claim 1 wherein the drug is a maytansinoid.

26. The method of claim 1 wherein the drug is an auristatin.

27. The method of claim 1 wherein the drug is MMAE.

28. The method of claim 1 wherein the drug is MMAF.

29. The method of claim 1 wherein the mass of each species of the antibody drug conjugate compounds is measured within 7.5 Da.

30. The method of claim 1 wherein the mass of each species of the antibody drug conjugate compounds is measured within 25 Da.

31. The method of claim 1 wherein the mass of each species of the antibody drug conjugate compounds is measured within 100 ppm of the theoretical value.

32. The method of claim 1, wherein the mixture comprises unconjugated antibodies.

33. The method of claim 1, wherein the step (d) comprises comparing the ion intensity of each species of the antibody drug conjugate compounds to the total ion intensity of the mixture.

34. The method of claim 1 further comprising quantitating a drug loading of the mixture.

* * * * *